(12) United States Patent
Kang et al.

(10) Patent No.: US 12,052,925 B2
(45) Date of Patent: Jul. 30, 2024

(54) METHOD AND DEVICE FOR DRIVING A PIEZOELECTRIC DEVICE

(71) Applicants: Liat Keng Kang, Singapore (SG); William Tan, San Gabriel, CA (US)

(72) Inventors: Liat Keng Kang, Singapore (SG); William Tan, San Gabriel, CA (US)

(*) Notice: Subject to any disclaimer, the term of this patent is extended or adjusted under 35 U.S.C. 154(b) by 978 days.

(21) Appl. No.: 17/033,781

(22) Filed: Sep. 26, 2020

(65) Prior Publication Data

US 2021/0020823 A1 Jan. 21, 2021

Related U.S. Application Data

(63) Continuation-in-part of application No. 15/004,920, filed on Jan. 23, 2016, now abandoned.

(60) Provisional application No. 62/907,428, filed on Sep. 27, 2019.

(51) Int. Cl.
| H01L 41/02 | (2006.01) |
| B05B 17/06 | (2006.01) |
| H10N 30/80 | (2023.01) |

(52) U.S. Cl.
CPC ....... *H10N 30/802* (2023.02); *B05B 17/0653* (2013.01)

(58) Field of Classification Search
CPC .................................................... H10N 30/802
USPC ................................................. 310/317, 367
See application file for complete search history.

(56) References Cited

U.S. PATENT DOCUMENTS

| 4,085,893 A | 4/1978 | Purley |
| 4,689,515 A | 8/1987 | Bendorf |
| 4,715,353 A | 12/1987 | Koike |
| 5,113,116 A | 5/1992 | Wilson |
| 6,278,218 B1 | 8/2001 | Madan |
| 7,034,800 B2 | 4/2006 | Nataksuka |
| 7,119,475 B2 | 10/2006 | Matsuzaki |
| 7,855,606 B2 | 12/2010 | Onuma |
| 9,149,588 B2 | 10/2015 | Gordon |
| 10,603,683 B2 | 3/2020 | Maeda |
| 2006/0082253 A1* | 4/2006 | Hara ................. H02N 2/062 |
| | | 310/317 |
| 2009/0065600 A1 | 3/2009 | Tranchant |
| 2009/0099485 A1 | 4/2009 | Sarvazyan |
| 2009/0295455 A1 | 12/2009 | Goodchild |
| 2010/0044460 A1 | 2/2010 | Sauzade |
| 2012/0046765 A1* | 2/2012 | Nikolic ............... B06B 1/0253 |
| | | 700/90 |
| 2020/0060337 A1 | 2/2020 | Liu |

FOREIGN PATENT DOCUMENTS

| CN | 102526848 A | 7/2012 |
| GB | 2107611 A | 5/1983 |

* cited by examiner

*Primary Examiner* — Derek J Rosenau

(57) ABSTRACT

There is presented a method for driving a piezoelectric device and an atomizer for atomizing a fluid, and an atomization method for a fluid using a piezoelectric device; the atomizer employs a piezoelectric device and circuitry that uses a switching voltage across the piezoelectric device at an operating frequency; sensing a sensed voltage corresponding to a phase of the piezoelectric device; and responsive to whether the sensed voltage is in phase or out of phase relative to the switching voltage, changing the operating frequency provided to the piezoelectric device, and the changing is one of: increasing the operating frequency by a first value, or decreasing the operating frequency by a second value.

20 Claims, 22 Drawing Sheets

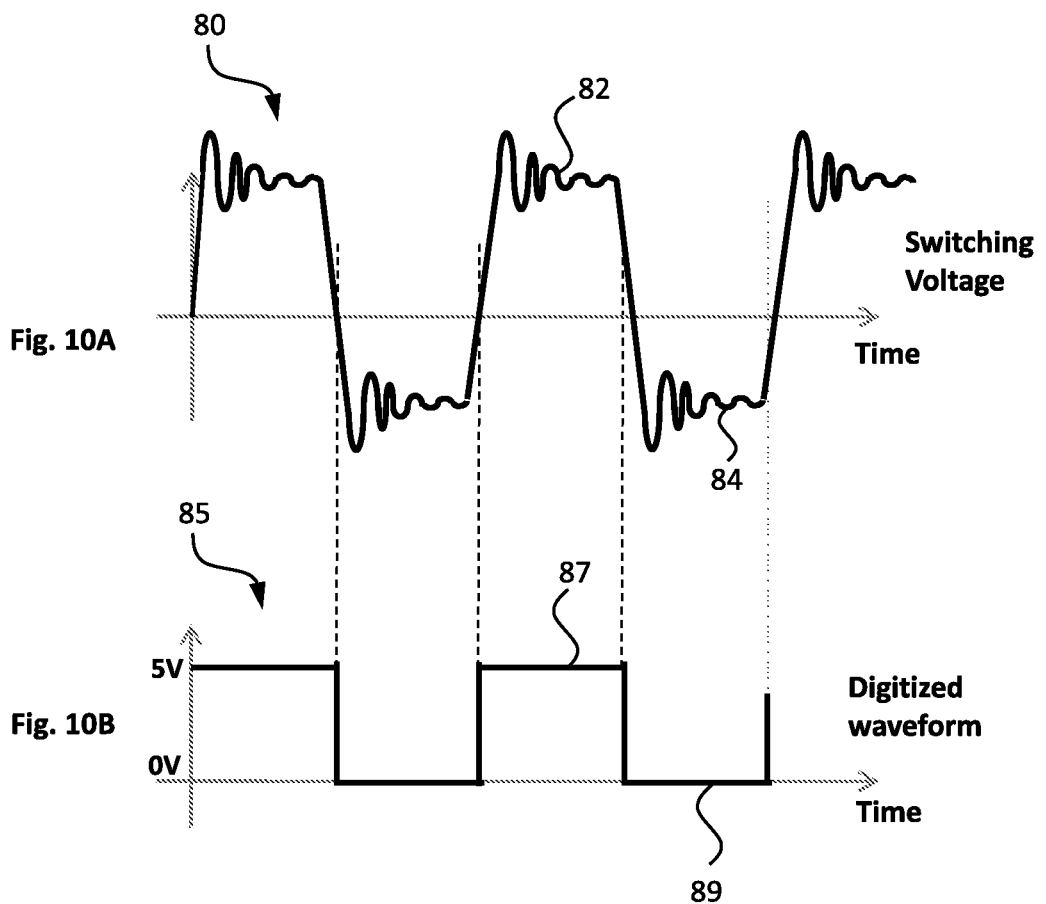
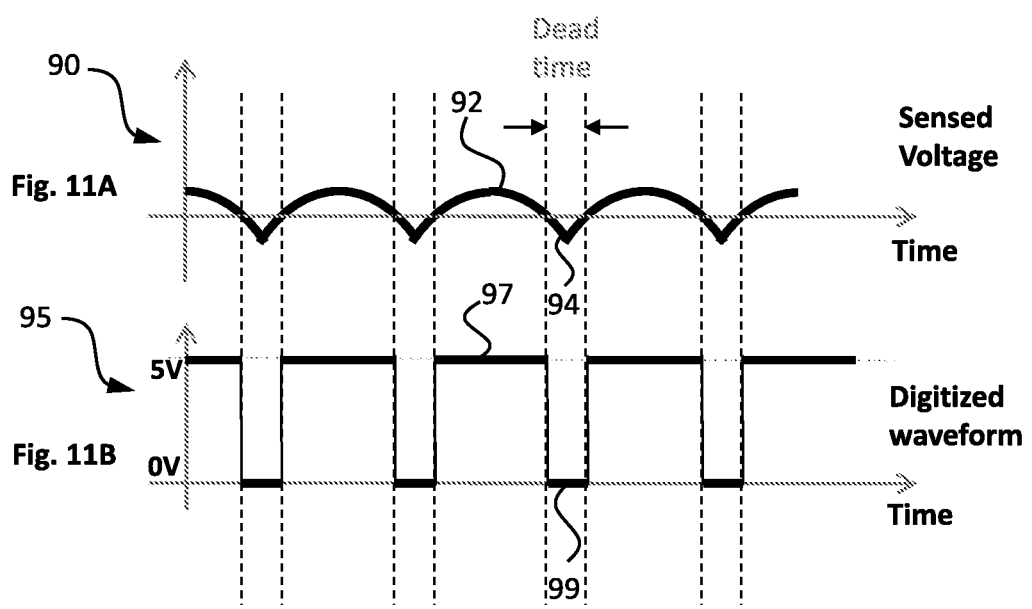

METHOD AND DEVICE FOR DRIVING A PIEZOELECTRIC DEVICE

PRIORITY CLAIM

This application claims the benefit of U.S. Provisional Patent Appl. No. 62/907,428, filed on Sep. 27, 2019; this application a continuation in part of U.S. patent application Ser. No. 15/004,920, filed on Jan. 23, 2016. This application is also related to U.S. Provisional Patent Appl. No. 62/314,380, filed on Mar. 28, 2016; U.S. Provisional Patent Appl. No. 62/343,086, filed May 30, 2016; U.S. Provisional Patent Appl. No. 62/106,852, filed on Jan. 23, 2015 and U.S. Provisional Patent Appl. No. 62/142,464, filed on Apr. 2, 2015. All listed applications are incorporated by reference in entirety.

FIELD OF INVENTION

Disclosed herein relates to the field of piezoelectric device, in particular a device for driving a piezoelectric device.

BACKGROUND

Atomization is useful for delivering medication, or other substances, directly to the human respiratory system. A piezoelectric transducer is used to agitate a liquid so that cavitation results, and droplets or micro-droplets of the liquid can be formed. It has been observed that the conventional piezoelectric transducer may not perform as desired when the liquid is oil-based or when the liquid is more viscous than water. In some cases, a liquid medication is made into a diluted water-based suspension, so as to enable its delivery by a nebulizer operating with a conventional piezoelectric transducer. In some cases, the liquid is intentionally heated to enable its vaporization. Understandably, such approaches can negatively impact the quality or efficacy of the liquid or medication.

Therefore, there remains a need for a device that can aerosolize or atomize a liquid, especially a liquid more viscous than water, preferably without involving intentional heating of the liquid.

SUMMARY

In one aspect, the present disclosure provides a method of driving a piezoelectric device, the method including: providing a switching voltage across the piezoelectric device at an operating frequency; sensing a sensed voltage corresponding to a phase of the piezoelectric device; and responsive to whether the sensed voltage is in phase or out of phase relative to the switching voltage, changing the operating frequency provided to the piezoelectric device, in which the changing is one of: increasing the operating frequency by a first value, and decreasing the operating frequency by a second value.

In one embodiment, the method further includes: converting the switching voltage to a switching voltage digital signal having at least one transition between two states; and using the at least one transition to trigger the sensing of the sensed voltage. In another embodiment, the method further includes: converting the sensed voltage to a sensed voltage digital signal; and comparing the switching voltage digital signal with the sensed voltage digital signal to determine whether the sensed voltage is in phase or out of phase relative to the switching voltage. The method may further include: periodically sensing the sensed voltage at a sampling frequency. Further, the sensed voltage may be in phase with the switching voltage when the sensed voltage digital signal is in a first state, and wherein the sensed voltage is out of phase with the switching voltage when the sensed voltage digital signal is in a second state. Optionally, the sensed voltage is across a resistive element operably coupled to the piezoelectric device. Alternatively, the sensed voltage is in phase with a current through the piezoelectric device. The method may further include: periodically sensing the sensed voltage at a sampling frequency. In another embodiment of the method, the operating frequency fluctuates about a variable median at a frequency corresponding to the sampling frequency, the variable median being dependent on a target frequency characterizing the piezoelectric device. An upper bound of the operating frequency may be equal or lower than the target frequency. A lower bound of the operating frequency may be equal or higher than the target frequency. Optionally, the target frequency is a resonance frequency of the piezoelectric device. In yet another embodiment, the method further includes: decreasing the operating frequency of the switching voltage when the sensed voltage is in phase relative to the switching voltage; and increasing the operating frequency of the switching voltage when the sensed voltage is out of phase relative to the switching voltage. Further, the method may further include: upon switching on the piezoelectric device, providing the switching voltage at an initial operating frequency, wherein the initial operating frequency is lower than a target frequency associated with the piezoelectric device.

In another embodiment, the method further includes: increasing the operating frequency of the switching voltage when the sensed voltage is in phase relative to the switching voltage; and decreasing the operating frequency of the switching voltage when the sensed voltage is out of phase relative to the switching voltage. The method may further include: upon switching on the piezoelectric device, providing the switching voltage at an initial operating frequency, wherein the initial operating frequency is higher than a target frequency associated with the piezoelectric device.

In an embodiment of the method, the first value is a predetermined value; and the second value is a predetermined value. Optionally, the first value is equal to or lower than a target frequency band of the piezoelectric device. Alternatively, the second value is equal to or lower than a target frequency band of the piezoelectric device. Optionally, the target frequency band is a resonance frequency band.

In another aspect, a device for driving a piezoelectric device include: an alternator coupled to the piezoelectric device, the alternator being configured to provide a switching voltage to drive the piezoelectric device; a controller coupled to the alternator, the controller being configured to control an operating frequency of the switching voltage; a sense load operably coupled to the piezoelectric device, wherein a sensed voltage across the sense load is configured to correspond to a phase of the piezoelectric device, wherein the controller is being configured to change the operating frequency responsively to the sensed voltage.

The device may further include: a logic device, the logic device being configured to cause the controller to change the operating frequency by a predetermined amount responsive to whether the sensed voltage is in phase or out of phase relative to the switching voltage. The device may be configured such that the sense load is a resistive element. The device may be configured such that the sensed voltage is in phase with a current through the piezoelectric device. The device may be configured such that the piezoelectric device includes a transformer coupled to a piezoelectric element, the transformer being configured to step up the switching voltage to drive the piezoelectric element. The device may further include: an analog digital converter, the analog digital converter being coupled to the logic device to convert the switching voltage to a switching voltage digital signal, in which the switching voltage signal has at least one transition between two states. The device may be configured such that the analog digital converter is configured to convert the sensed voltage to a sensed voltage digital signal, the sensed digital voltage signal having at least one transition between two states. The device may be configured such that the analog digital converter is an operational amplifier comparator.

In one embodiment, the controller is configured to change the operating frequency at a sampling frequency corresponding to the operating frequency. In one embodiment, the logic device is a digital flip flop, configured to receive the switching voltage and the sensed voltage as input. In one embodiment, the sensed voltage is sensed at a transition of the switching voltage. The sensed voltage may be sensed at a positive transition of the switching voltage. The sensed voltage may be sensed at multiple positive transitions of the switching voltage. In another embodiment, the sensed voltage may be sensed at a negative transition of the switching voltage. The sensed voltage may be sensed at multiple negative transitions of the switching voltage. The first value may be equal to the second value. The first value may be equal to or lower than a target frequency band of the piezoelectric device. The second value may be equal to or lower than a target frequency band of the piezoelectric device. The alternator may be a full-bridge configured to produce a switching voltage corresponding to a square waveform. The alternator may be a push-pull configuration configured to produce a switching voltage corresponding to a square waveform. The alternator may be couplable to a battery.

According to one aspect, an atomizer for atomizing a fluid includes: a piezoelectric device operable by a switching voltage; a sense load operably coupled to the piezoelectric device so that a sensed voltage across the sense load corresponds to a phase of the piezoelectric device; and a controller coupled to the piezoelectric device and the sense load, the controller being configured to sense the sensed voltage and to change the operating frequency responsive to the sensed voltage. According to another aspect, an atomizer for atomizing a fluid, the atomizer is being configured to: provide a switching voltage across a piezoelectric device at an operating frequency; sense a sensed voltage corresponding to a phase of the piezoelectric device; and, responsive to the sensed voltage, change the operating frequency of the switching voltage. According to either of these aspects, the atomizer may be configured to provide a non-intermittent stream of atomized fluid over a period of operation, and wherein the operating frequency is varied by a predetermined amount over the period of operation. The atomizer may be configured to change the operating frequency at time intervals. The atomizer may be configured to sense the sensed voltage at a sensing frequency corresponding to the time intervals. The atomizer may be configured such that a change in the operating frequency is equal to or less than a target frequency band. The operating frequency may be intermittently within a target frequency band of the piezoelectric device.

According to one aspect, a device for atomizing a fluid using a piezoelectric device, the device is configured to: provide a switching voltage to the piezoelectric device; change an operating frequency of the switching voltage by an amount that brings the operating frequency within a target frequency band of the piezoelectric device; and change the operating frequency of the switching voltage by the amount that brings the operating frequency out of the target frequency band. The amount of change of the operating frequency may be equal to or less than a range of the target frequency band. The device may be configured such that, when the operating frequency is within the target frequency band of the piezoelectric device, the operating frequency corresponds to the piezoelectric device being at resonance. The device may be further configured to: repeatedly and alternately change the operating frequency of the switching voltage to within the target frequency band, and change the operating frequency out of the target frequency band.

An atomizer as above, wherein the fluid has a viscosity of at least 5 centipoises.

The above and other features and advantages of the invention will be described below with reference to exemplary embodiments as illustrated in the accompanying drawings.

BRIEF DESCRIPTION OF DRAWINGS

FIG. 10A shows an example of a switching voltage according an embodiment;

FIG. 10B shows a digitalized example of the switching voltage according to FIG. 10A;

FIG. 11A shows an example of a sensed voltage according an embodiment;

FIG. 11B shows a digitalized example of the sensed voltage according to FIG. 10A;

PARTS LISTING

Figure 1:
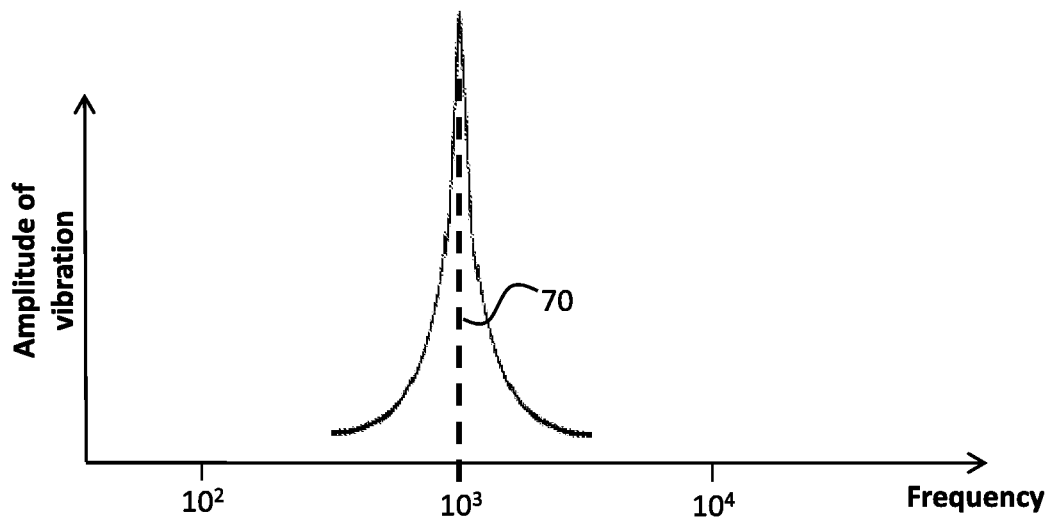
FIG. 1 is an amplitude-frequency plot illustrating a relationship between an amplitude of vibration of a piezoelectric element and its operating frequency.

Apparatus or Atomizer 40
Power source, battery or DC power source 50
Piezoelectric device 60
Transformer 62
Piezoelectric element 64
Center-tapped transformer 66
Target frequency or plot 70
   Target frequency band 70a
   an upper limit 70b and
   a lower limit 70c
Operating frequency 72
   Increasing 72a the operating frequency
   Decreasing 72b the operating frequency
Ideal target frequency 74
Alternating current (AC) switching voltage or switching voltage 80
Current 80a, 80b
Switching voltage digital signal 85
Higher voltage 87
Lower voltage 89
Sensed voltage 90, 94
Sensed voltage digital signal 95
Lower voltage state 99
Driving device 100
Alternator 110
Controller 120
Sense load 130
Logic device 140
Driving device 200
Full-bridge 210 (H-bridge)
Switches 212/214/216/218
Controller 220
Sense Load 230
Logic device 240
Analog-to-digital converters (ADC) 262/264
Driving device 300
Operational amplifier comparator 362/364
Driving device 400
Half-bridge 410
Switches 412/414
Controller 420
Sense load 430
Driving device 500
Full-bridge 510
Micro controller unit (MCU) 520
Sense load 530
Method 700 of driving a piezoelectric device
Operating frequency (710),
A phase of the piezoelectric device (720).
Changing the operating frequency provided to the piezoelectric device (730)
Switching voltage digital signal (740)
Sensed voltage digital signal (750).
Sensed voltage digital signal (760)
Sampling frequency (770).
Voltage 810a/810b/810c
Current 820a/820b/820c
Current 840 of piezoelectric device driven by another device
   periodic drops 840a and
   recoveries 840b
Transition 850
Positive (rising) transitions 850a (of the switching voltage digital signal 85
Negative (falling) transitions 850b of the switching voltage digital signal 85
Positive transitions 852a/852b/852c
Positive transitions 854a/854b
Positive transitions 856a/856b/856c
Sampling Interval (of time) 950

DETAILED DESCRIPTION

In the present disclosure, a piezoelectric device refers to a device configured to exhibit piezoelectric behavior in which a mechanical stress/deformation is generated in response to an application of an electrical field. According to embodiments of the present disclosure, the piezoelectric device may include one or more elements and/or materials that is/are configured to exhibit piezoelectric behavior. It can be appreciated that piezoelectric devices according to embodiments of the present disclosure may be used in various applications, including but not limited to atomizers, nebulizers, ultrasound devices, etc. For the sake of brevity, the one or more elements and/or materials that can exhibit piezoelectric behavior is hereinafter referred to as a piezoelectric element. In one exemplary application, a piezoelectric device according to an embodiment of the present disclosure is configured as an atomizer suitable for use with a fluid. The fluid may be in the form of a single chemical compound, or it may be in the form of a solution, suspension, mixture, etc., of more than one chemical substance. The piezoelectric device is configured to cause vibration of a piezoelectric element with the piezoelectric element being in contact with the fluid, or with the piezoelectric element being configured to transmit energy to the fluid.

FIG. 1 is an example of an amplitude-frequency plot illustrating a relationship between an amplitude of vibration of a piezoelectric element and an operating frequency of an electrical field applied to the piezoelectric element. It can be appreciated that if the piezoelectric element is driven at an operating frequency close to or at its resonant frequency 70 (in this case, 103 Hz, as an example), the piezoelectric element will exhibit vibration at a peak amplitude. The amplitude of vibration drops quickly from the peak amplitude if the operating frequency deviates from the resonant frequency 70, which results in a significant decrease in the efficiency of the apparatus.

The piezoelectric element may be subjected to varying operating conditions such as changes in temperature, internal heat build-up, etc., such that there is a tendency for the resonant frequency of the piezoelectric element to drift away from the initial resonant frequency 70. It is a challenge to set the operating frequency at the resonant frequency at any instant since the latter varies non-linearly over any period of time when the piezoelectric element is in operation. When the piezoelectric element is part of a piezoelectric device, it is observed that the relationship between the amplitude of vibration and the operating frequency is even more unpredictable.

Figure 2:
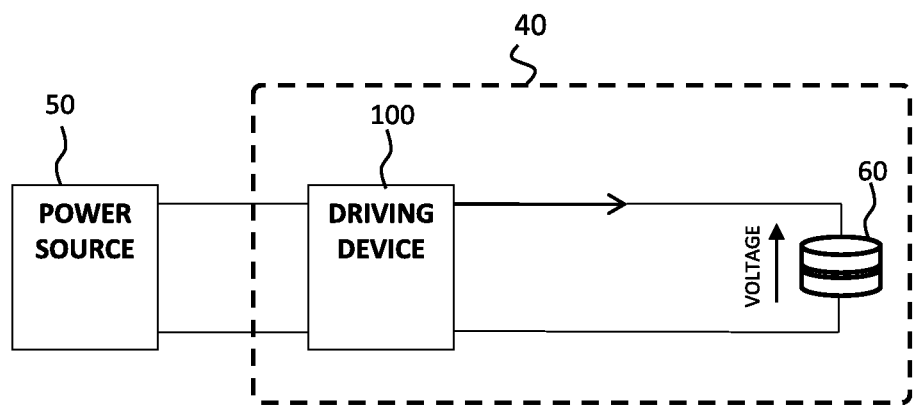
FIG. 2 is a schematic diagram showing an apparatus according to an embodiment of the present disclosure.

FIG. 2 illustrates an exemplary schematic circuit of an apparatus configured to operate on power received from a power source 50, the apparatus 40 including a piezoelectric device 60 and a driving device 100, in accordance with an embodiment of the present disclosure. The piezoelectric device 60 includes at least one piezoelectric element. The driving device 100 is configured to operate or drive the piezoelectric device 60 by providing an electrical field alternating at an operational frequency. The driving device 100 may be said to operate or drive the piezoelectric device by providing a voltage across the piezoelectric device.

Figure 3A:
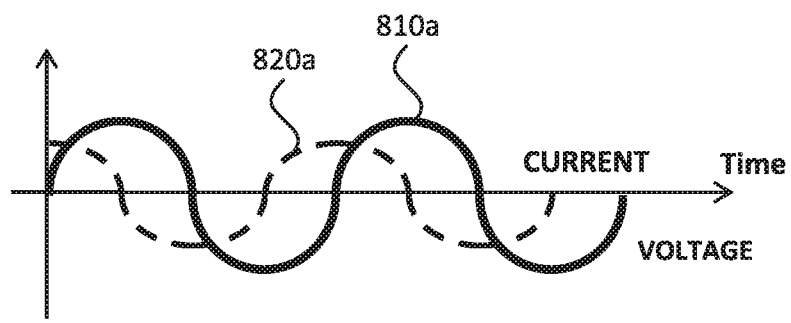
FIG. 3A is an amplitude-time plot illustrating a switching voltage leading a current driving a piezoelectric device.
Figure 3B:
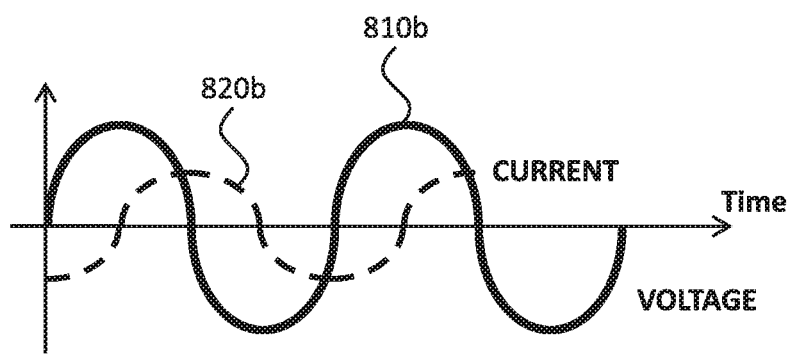
FIG. 3B is an amplitude-time plot illustrating a switching voltage lagging a current driving a piezoelectric device.
Figure 3C:
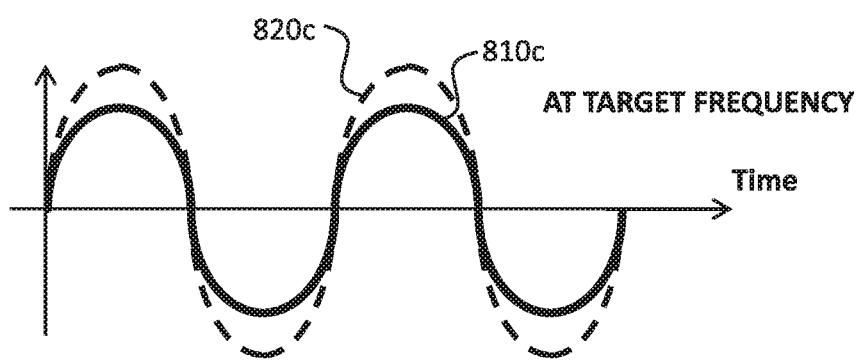
FIG. 3C is an amplitude-time plot illustrating a switching voltage in phase with a current driving a piezoelectric device.

According to embodiments of the present disclosure, the apparatus of FIG. 2 may be configured so that FIGS. 3A, 3B, and 3C are amplitude-time plots illustrating a relationship between a voltage 810a/810b/810c across the piezoelectric device 60 and a current 820a/820b/820c drawn by the piezoelectric device 60. FIG. 3A shows a situation where the operating frequency is lower than a target frequency, in which the voltage 810a leads the current 820a. FIG. 3B shows a situation where the operating frequency is higher than the target frequency, in which the voltage 810b lags the current 820b. In both of these instances, the voltage 810a/810b across the piezoelectric device and the current 820a/820b drawn are said to be not in phase. The apparatus is configured to drive the piezoelectric device at or near the target frequency. The resulting voltage 810c and current 820c waveforms are said to be in phase, or in other words in sync, as illustrated by FIG. 3C.

Figure 4A:
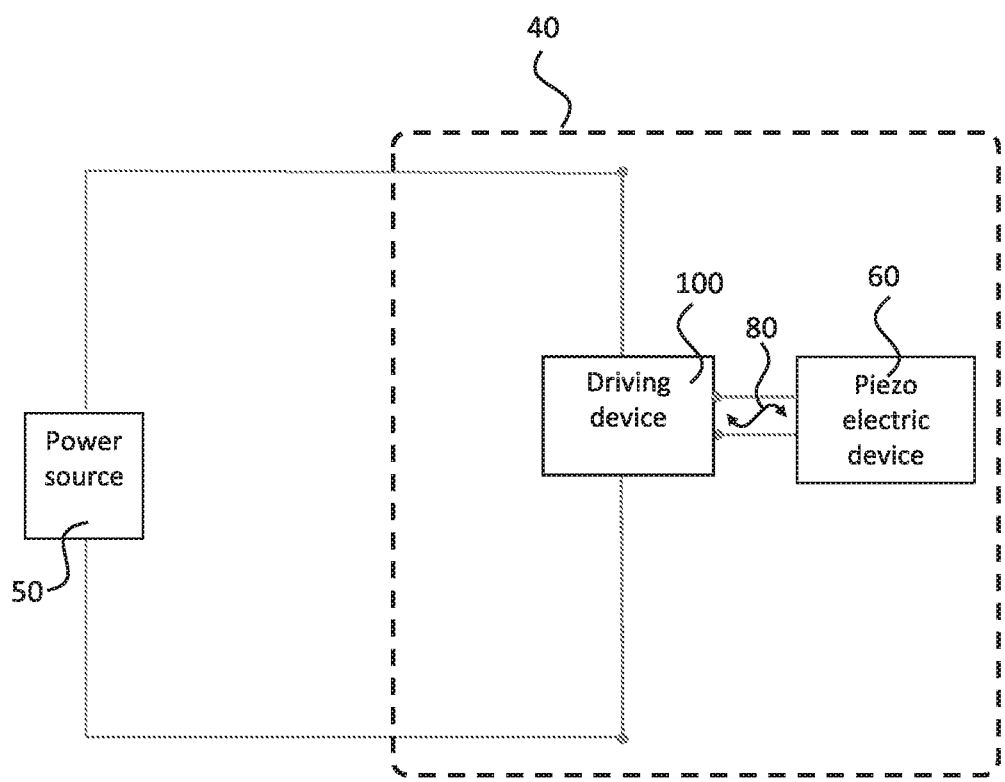
FIG. 4A is a schematic diagram illustrating an atomizer according to an embodiment.

FIG. 4A illustrates, by way of a schematic block diagram, an embodiment of an atomizer 40 which may be used to atomize a fluid, such as a viscous fluid. The atomizer 40 includes a piezoelectric device 60 and a driving device 100. The driving device 100 is configured to drive the piezoelectric device 60. The driving device 100 is configured to provide a switching voltage to drive the piezoelectric device 60. The driving device is configured to control an operating frequency of the switching voltage. A power source 50 may be coupled to the driving device 100 to enable operation of the atomizer 40. In an example, the power source 50 includes a direct current (DC) power source, such as a battery. The atomizer 40 may be configured as a portable and/or handheld device, and the driving device 100 may be configured to convert the DC power source to an alternating current (AC) switching voltage 80 suitable for driving the piezoelectric device 60 to effect atomization of a viscous fluid. The driving device 100 may be configured to provide the switching voltage 80 at an operating frequency enabling the piezoelectric device 60 to be driven at or near a target frequency. In another example, the power source 50 is configured as an AC power source. The atomizer 40 may include a driving device 100 configured to convert the AC power source to an alternating current (AC) switching voltage 80 suitable for driving the piezoelectric device 60 to effect atomization of a viscous fluid. The driving device 100 may be configured to provide the switching voltage 80 at an operating frequency enabling the piezoelectric device 60 to be driven at or near a target frequency.

According to an exemplary embodiment, the atomizer 40 is configured to atomize a viscous fluid, for example, a fluid with a viscosity equal to or above 5 centipoise (cp). In another example, the atomizer 40 is configured to atomize water, a water-based solution, an oil, an oil-based solution, or a mixture thereof.

Figure 4B:
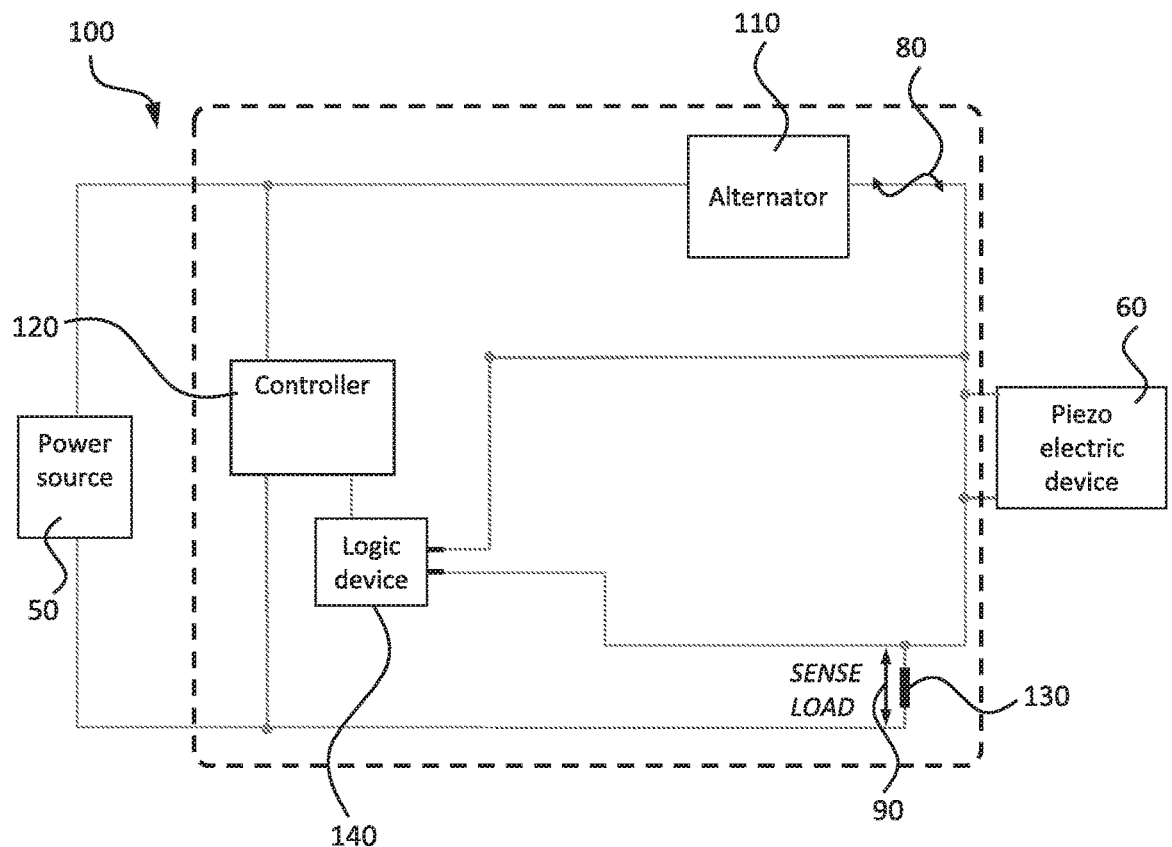
FIG. 4B is a schematic diagram illustrating a device for driving a piezoelectric device according to an embodiment.

An embodiment of a driving device 100 is illustrated in FIG. 4B. The driving device 100 includes an alternator 110, a controller 120 coupled to the alternator 110, a sense load 130 coupled to the piezoelectric device 60, and a logic device 140 coupled between the controller and the sense load 130. The alternator 110 is configured to convert electrical power from a power source 50 to a switching voltage 80. The switching voltage 80 may be provided to drive the piezoelectric device 60. As an example, a direct current (DC) voltage from the power source 50 is converted and provided to the piezoelectric device 60 as an alternating current (AC) switching voltage 80. By way of controlling the alternator 110, the controller 120 is configured to control an operating frequency of the switching voltage 80. Further, as switching voltage 80 is provided to the piezoelectric device 60, a sensed voltage 90 across the sense load 130 may be sensed. The logic device 140 may be configured to sense or sample the sensed voltage 90 and, responsive to the sensed voltage 90, the logic device 140 may be configured to instruct the controller 120 to change the operating frequency. The sensed voltage 90 may be taken to correspond to a phase or a state of the piezoelectric device 60. As an example, the sense voltage 90 may be taken to correspond to and be in phase with a current through the piezoelectric device 60, that is, the sense voltage 90 may be taken to be reflective of a state of the piezoelectric device 60. Alternatively, the sense voltage 90 may be taken to correspond to an operating state of the piezoelectric device 60, such as a vibration state of the piezoelectric device 60.

For example, the logic device 140 may be configured to instruct the controller 120 to either increase or decrease the operating frequency provided to the piezoelectric device, responsive to whether the sensed voltage 90 is in phase or out of phase relative to the switching voltage 80. Further and optionally, the logic device 140 may be configured to receive the switching voltage 80 as an input. The logic device 140 may be configured to receive input from both the switching voltage 80 and the sensed voltage 90 and, based on a logic rule, to determine whether to increase or to decrease the operating frequency. As an example, the logic device 140 may be configured to instruct the controller to decrease the operating frequency when the sensed voltage 90 is in phase with the switching voltage 80. The logic device 140 may be configured to instruct the controller to increase the operating frequency when the sensed voltage 90 is out of phase with the switching voltage 80.

Figure 5:
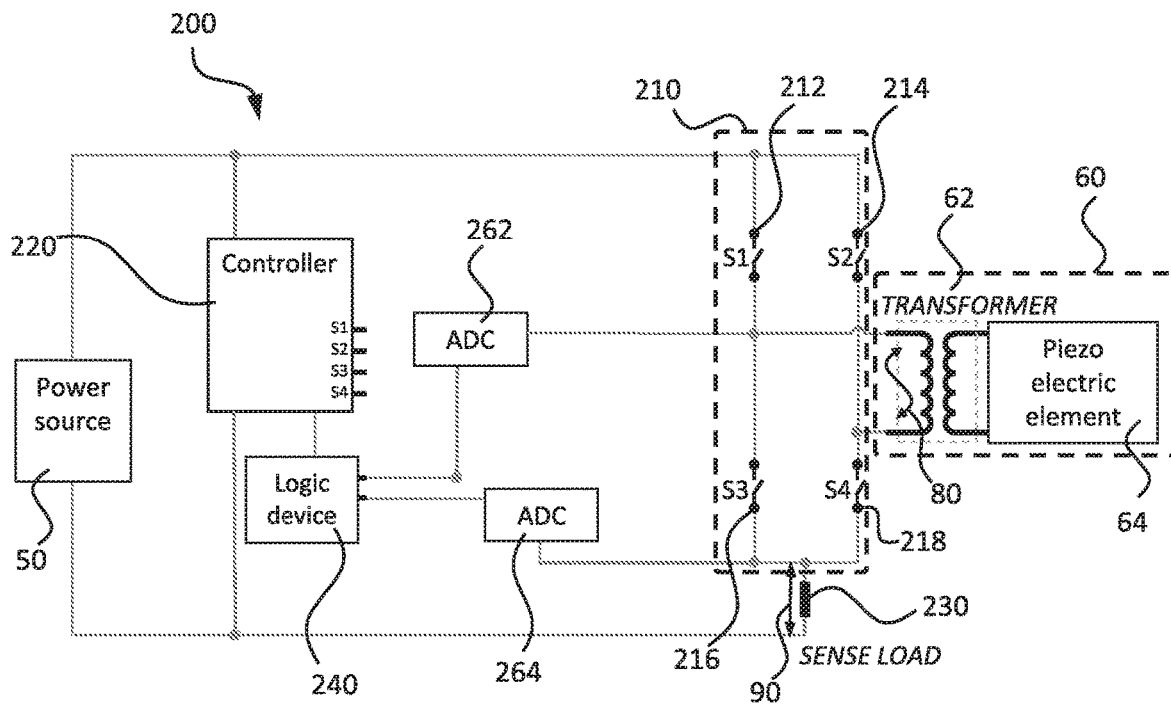
FIG. 5 is a schematic diagram illustrating a device for driving a piezoelectric device according to another embodiment.

FIG. 5 schematically illustrates a driving device 200 in accordance with another embodiment of the present disclosure. The driving device 200 may be coupled to a power source 50 and a piezoelectric device 60. The piezoelectric device 60 includes one or more piezoelectric element 64. Optionally, the piezoelectric device 60 may include a transformer 62. The transformer 62 may be configured to step up a switching voltage 80 to a voltage suitable for driving the piezoelectric element 64. In this embodiment, the driving device 200 includes an alternator, in which the alternator includes a full-bridge 210 (H-bridge) formed from switches 212/214/216/218. The full-bridge 210 is operably coupled to and controllable by a controller 220. A logic device 240 is coupled to the controller 220. The switches 212/214/216/218 may include Metal Oxide Semiconductor Field Effect Transistors (MOSFETs) or other suitable electronic switching devices such as Bipolar Transistors, IGBT, SCR, TRIAC, DIAC, etc., or a combination of devices selected therefrom. In one example, the alternator includes a plurality of MOSFETs. In one example, the alternator is configured with low voltage devices such as MOSFETs so that the driving device is operable with a conventional battery serving as the power source, while enabling sufficient vibration by the piezoelectric element. The controller 220 is configured to control the opening and closing of the switches 212/214/216/218, thereby converting a direct current (DC) voltage from the power source 50 into an alternating current (AC) switching voltage 80 to be provided to drive the piezoelectric device 60.

Figure 6A:
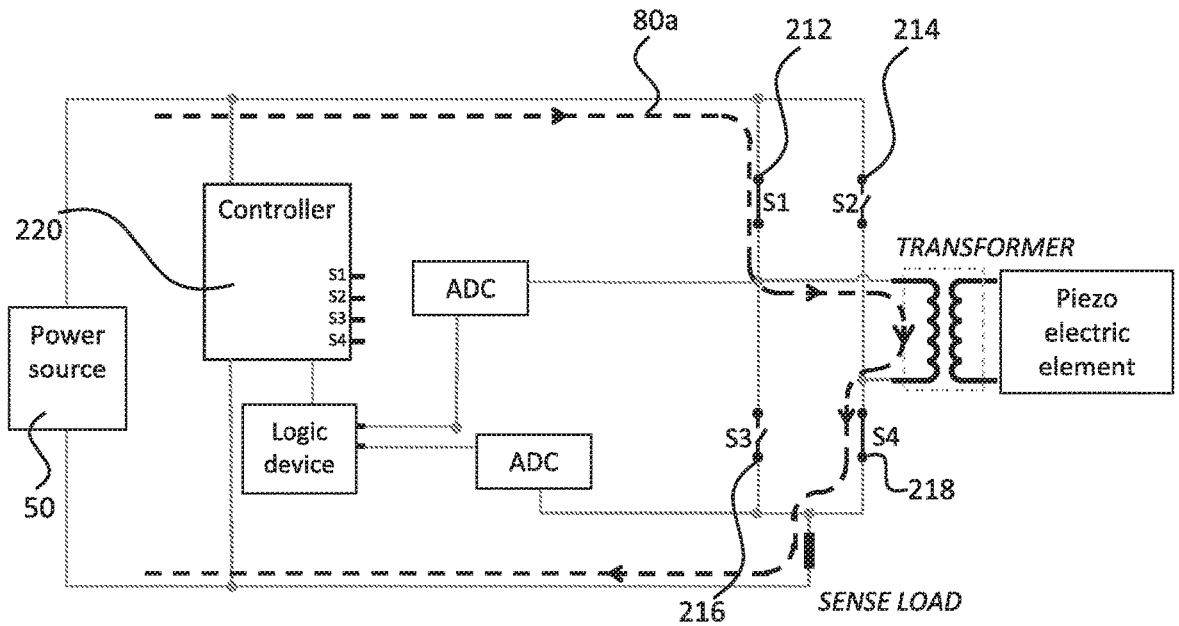
FIG. 6A is a schematic diagram illustrating a current flow through the device according to the embodiment of FIG. 5.
Figure 6B:
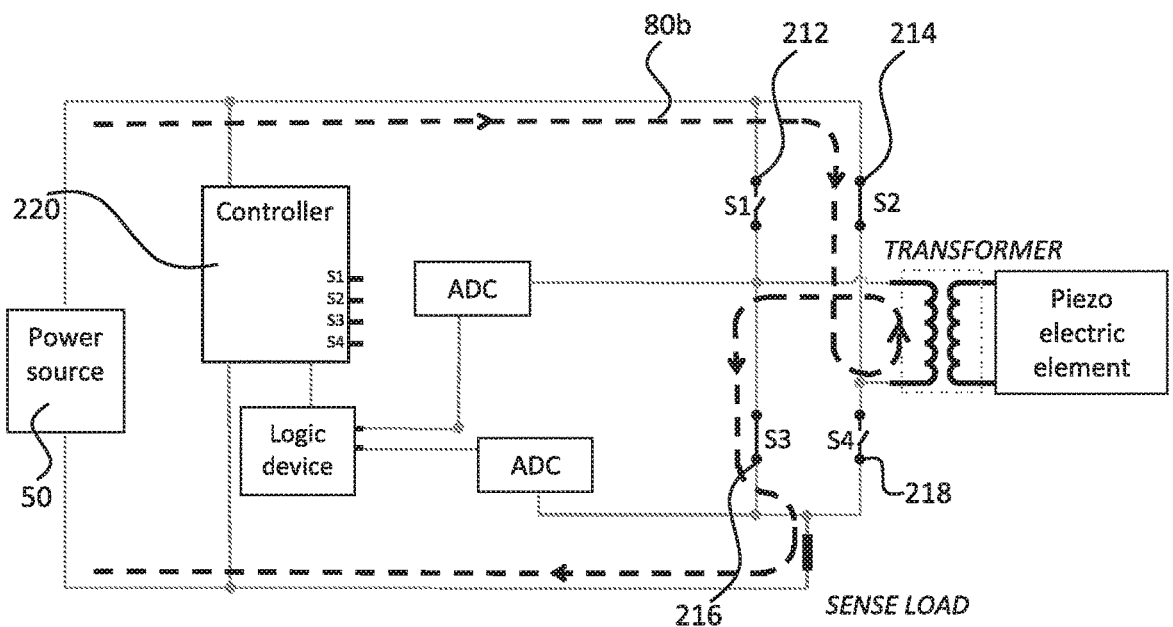
FIG. 6B is a schematic diagram illustrating the current flow through the device in another direction according to the embodiment of FIG. 6A.

FIGS. 6A and 6B illustrate driving device of FIG. 5 in operation. Referring to FIG. 6A, switches 212 and 218 are closed while switches 214 and 216 are opened in a first operational mode. Current 80a due to a switching voltage 80 is in a first direction through/in the transformer 62. In a second operational mode, as shown in FIG. 6B, switches 212 and 218 are opened while switches 214 and 216 are closed. The current 80b due to switching voltage 80 is in a second direction through/in the transformer 62, in which the second direction is opposite to the first direction. The driving device is configured to alternate between the first operational mode and the second operational mode, thereby providing a switching voltage 80 across the piezoelectric device, in which the switching voltage 80 is an AC voltage. One example of the switching voltage 80 that may be provided is shown in FIG. 10A. In an example, the switching voltage 80 may be or may approximate a square waveform. In an example, by controlling the switches 212/214/216/218, controller 220 is able to convert a DC voltage from the power source 50 to an AC switching voltage 80 across the piezoelectric device 60. Additionally, the controller 220 may be configured to vary an operating frequency of the switching voltage 80. The controller 220 may be configured to controllably vary the frequency of switching between the first operational mode and the second operational mode, in which the frequency corresponds to an operational frequency of the switching voltage 80. The controller 220 may be configured to controllably vary the rate of opening and closing of the switches 212/214/216/218 and thereby vary the operating frequency of the switching voltage 80.

Still referring to FIG. 5, drive device 200 may further include one or more analog-to-digital converters (ADC) 262/264. An ADC may be coupled to the full-bridge 210 so as to provide a digital signal 85 based on the switching voltage 80, as shown by FIG. 10A and FIG. 10B. An ADC may be coupled to a sense load 230, in which the sense load 230 is coupled to the piezoelectric device 60. The sense load 230 is configured such that a sensed voltage 90 across the sense load 130 can be determined. An ADC may be coupled to the sense load 230 so as to provide a digital signal 95 based on the sensed voltage 90, as illustrated by FIG. 11A and FIG. 11B. The driving device 200 may be configured so that the sensed voltage 90 corresponds to a phase of the piezoelectric device 60. As an example, the sense load 230 includes a pure resistive element. As shown in FIGS. 6A and 6B, the driving device may be configured so that current 80a/80b passes through the sense load 230 in the same direction whether the driving device or the bridge is operating in the first operational mode or in the second operational mode. Referring to FIG. 11A, as an example of a sensed voltage 90 across the sense load 230, the sensed voltage 90 across the sense load may be configured as generally positive, with negative portions of the sensed voltage 94 corresponding to dead time of the full-bridge. The ADC 262 and ADC 264 are respectively configured to convert a switching voltage 80 and a sensed voltage 90 into corresponding digital waveforms.

FIG. 10A illustrates an example of a switching voltage 80 and FIG. 10B illustrates an example of a corresponding switching voltage digital signal 85 transiting between two states. In this example, the driving device includes a circuit configured to derive the switching voltage digital signal 85 from the switching voltage 80, such as by converting the switching voltage 80 into a digitalized signal. For example, positive portions of the switching voltage 82 may be digitalized to a higher voltage 87, i.e., 5V (Volts), while negative portions of the switching voltage 84 may be digitalized to a lower voltage 89, i.e., 0V. In another example, the circuit is configured to convert the switching voltage signal 80 into a signal 85 characterized by a square waveform. It can be appreciated that the square waveform 85 may be described in terms of a higher voltage state 87 and a lower voltage state 89, in which the higher voltage state is characterized by a voltage value larger than that of the lower voltage state. The voltage values shown in FIG. 10B are merely for the purpose of illustration. The voltage value associated with the lower voltage state need not be 0V; the voltage value associated with the higher voltage state need not be 5V. It can further be appreciated that the switching voltage digital signal 85 corresponds to the switching voltage 80. In one example, the switching voltage digital signal 85 is characterized by a waveform that provides rising edges at a frequency corresponding to the frequency of the switching voltage 80. In another example, the switching voltage digital signal 85 is characterized by a waveform that provides falling edges at a frequency corresponding to the frequency of the switching voltage 80.

FIG. 11A illustrates an example of a sensed voltage 90 and FIG. 11B illustrates a sensed voltage digital signal 95 corresponding to the sensed voltage 90. In this example, the driving device includes a circuit configured to derive the sensed voltage digital signal 95 from the sensed voltage 90, such as by converting the sensed voltage 90 into a digitalized signal. For example, positive portions of the sensed voltage 92 are digitalized to a higher voltage 97, i.e., 5V, while negative portions of the sensed voltage 94 are digitalized to a lower voltage 99, i.e., 0V. These digital signals 85/95 act as input to the logic device 240. In another example, the circuit is configured to convert the sensed voltage signal 90 into a signal 95 characterized by a square waveform. It can be appreciated that the square waveform 95 may be described in terms of a higher voltage state 87 and a lower voltage state 89, in which the higher voltage state is characterized by a voltage value larger than that of the lower voltage state. The voltage values shown in FIG. 11B are merely for the purpose of illustration. The voltage value associated with the lower voltage state need not be 0V; the voltage value associated with the higher voltage state need not be 5V. It can further be appreciated that the sensed voltage digital signal 95 corresponds to the sensed voltage 90. In one example, the sensed voltage digital signal 95 is characterized by a waveform that provides a voltage state 99 at a frequency corresponding to the frequency of the sensed voltage 90. In another example, the sensed voltage digital signal 95 is characterized by a waveform that provides a voltage state 99, in which the voltage state 99 corresponds to a portion of the sensed voltage that is lower than a threshold voltage. In the example illustrated by FIG. 11A and FIG. 11B, the circuit is configured such that the threshold voltage is 0V, and the sensed voltage digital signal 95 includes a lower voltage state 99 that corresponds to the negative portion 94 of the sensed voltage 90. In another example, the sensed voltage digital signal 95 includes a series of signal pulses, in which consecutive signal pulses are spaced apart by an interval, each of the intervals being concurrent (in time) with the sensed voltage being lower than a threshold voltage.

Figure 7:
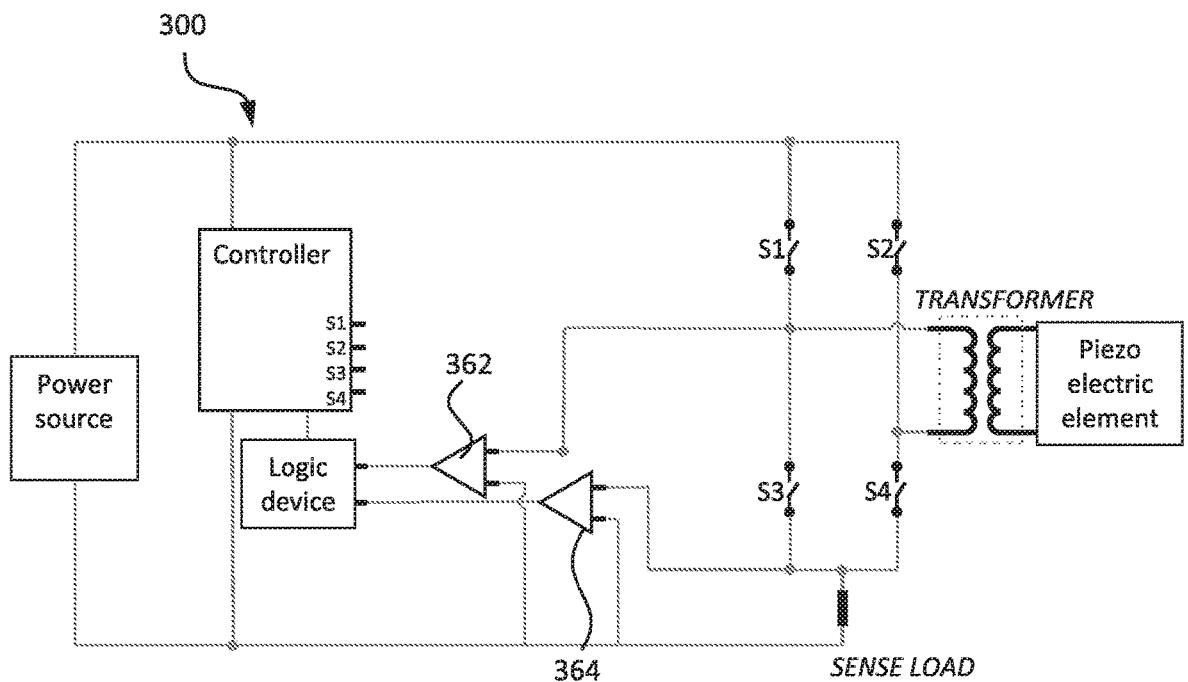
FIG. 7 is a schematic diagram illustrating a device for driving a piezoelectric device according to another embodiment.

Referring to FIG. 7, in another embodiment of a driving device 300, either of or both of the ADCs may be configured in the form of an operational amplifier comparator 362/364. The operational amplifier comparator is configured so that positive portions of a voltage are amplified and converted to an upper saturation voltage of the operational amplifier comparator, while negative portions of a voltage are amplified and converted to a lower saturation voltage of the operational amplifier comparator. As an example, FIG. 10A and FIG. 10B illustrate the provision of the operational amplifier comparator 362, with an upper saturation voltage of 5V and a lower saturation voltage of 0V, configured to convert the switching voltage 80 into a switching voltage digital signal 85. In another example, FIG. 11A and FIG. 11B, illustrate the provision of the operational amplifier comparator 364, with an upper saturation voltage of 5V and a lower saturation voltage of 0V, to convert the sensed voltage 80 into a sensed voltage digital signal 95.

Figure 8A:
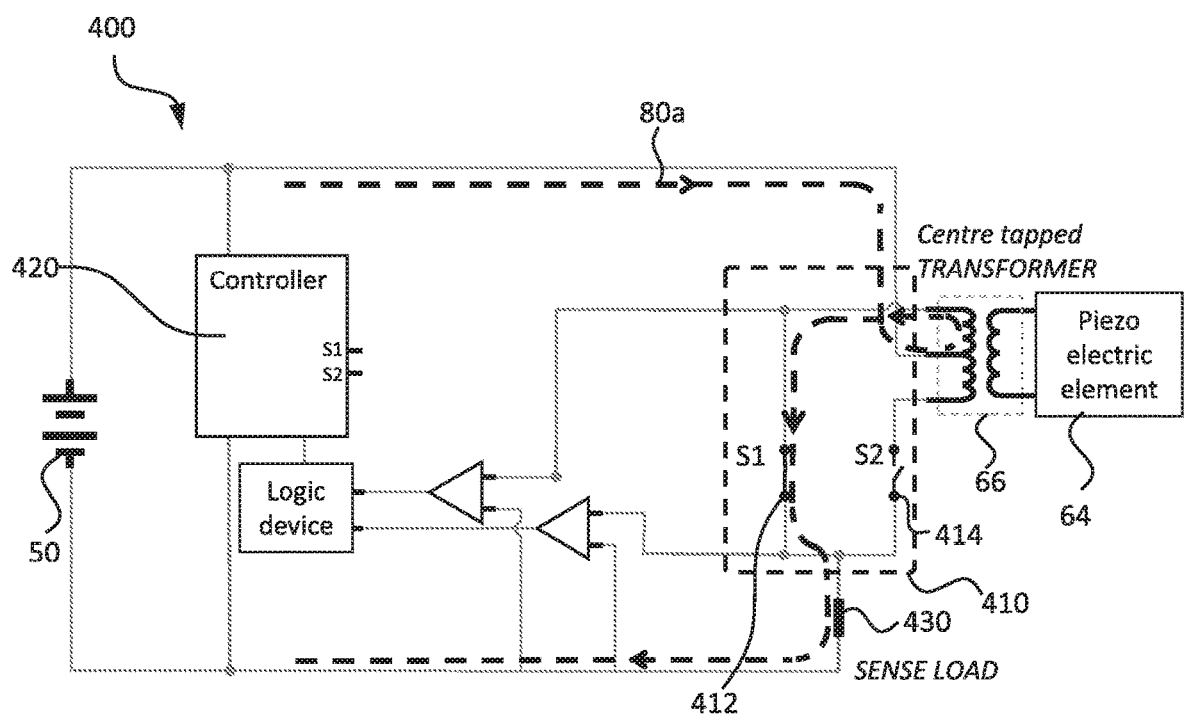
FIG. 8A is a schematic diagram illustrating a current flow through a device for driving a piezoelectric device according another embodiment.
Figure 8B:
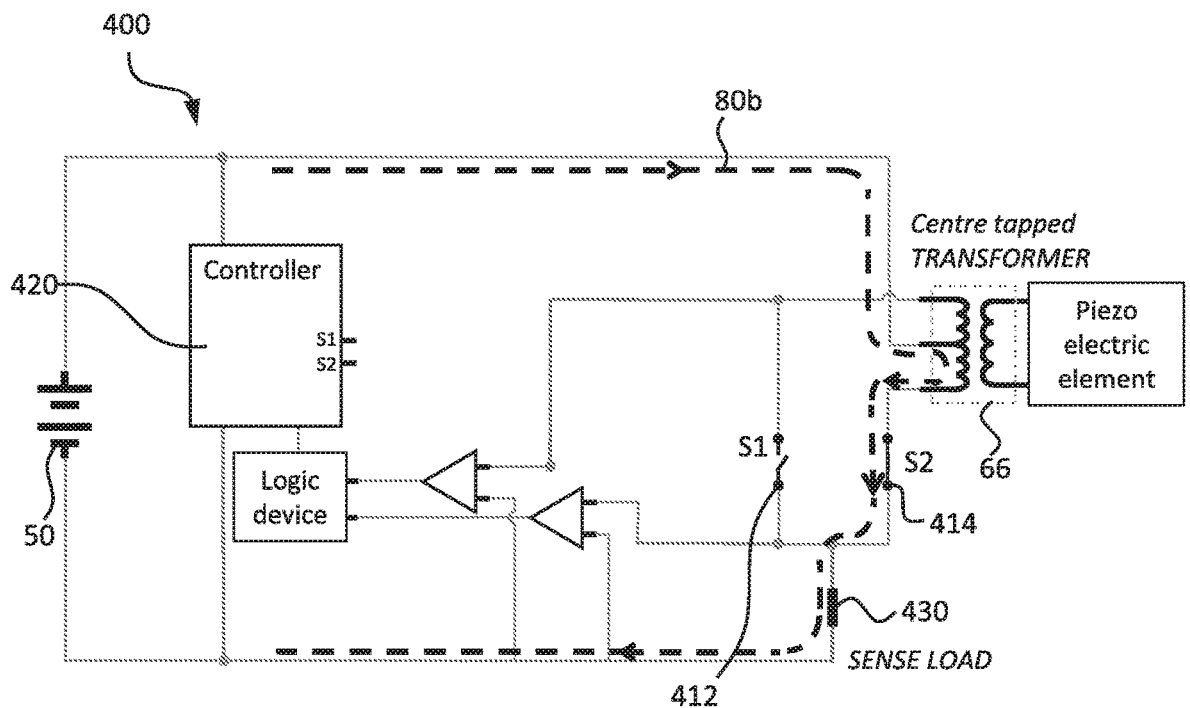
FIG. 8B is a schematic diagram illustrating the current flow through the device in another direction according to the embodiment of FIG. 8A.

Referring to FIGS. 8A and 8B, an embodiment of a driving device 400 includes a half-bridge 410, such as one formed from switches 412/414. A controller 420 is configured to control the opening and closing of the switches 412/414, thereby converting a direct current (DC) voltage from a power source 50 into an alternating current (AC) switching voltage 80, the switching voltage 80 being provided to a piezoelectric device 60. In this embodiment, the power source 50 may be a battery source and the piezoelectric device 60 includes a center-tapped transformer 66 and piezoelectric element 64.

Referring to FIG. 8A, when the switch 412 is closed while switch 414 is opened, a current 80a due to the switching voltage flows through a first portion of the center tapped transformer 66 in a first direction. Conversely, as shown in FIG. 8B, when the switch 412 is opened while switch 414 is closed, the current 80b flows through a second portion of the center tapped transformer 66, in a second direction which is opposite to the first direction. By controlling the switches 412 and 414, the controller 420 is able to convert a DC voltage from the power source 50 to an AC switching voltage across the center tapped transformer. Additionally, the controller 420 controls the rate of opening and closing of the switches 412/414 thereby varying an operating frequency of the switching voltage. The driving device is configured such that in operation the current flows through the sense load 430 in the same direction, regardless of the direction of current flow in the transformer.

Figure 9:
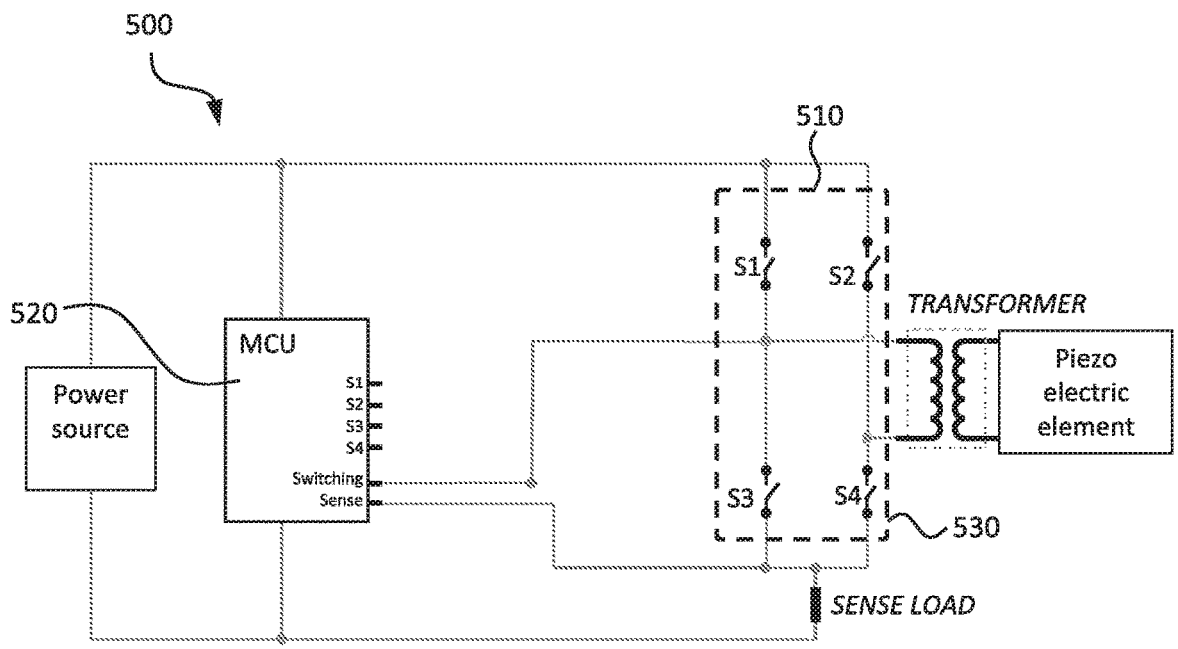
FIG. 9 is a schematic diagram illustrating a device for driving a piezoelectric device according to another embodiment.

From the examples described above, it can be appreciated that there are various ways of implementing embodiments of the present disclosure. For example, the driving device may be configured to provide digital signals 85/95 to the logic device 240, in which the digital signals include a switching voltage digital signal and a sensed voltage digital signal, and in which the switching voltage digital signal corresponds to a switching voltage provided to drive a piezoelectric device, and in which the sensed voltage digital signal corresponds to a sensed voltage. The driving device may be further configured to use the output from the ADCs 262/264 as input to a logic device 240. The logic device 240 may be configured such that, responsive to input received, the logic device 240 instructs the controller 220 to change the operating frequency of the switching voltage 80. FIG. 9 shows an alternative embodiment in which a driving device 500 includes a micro controller unit (MCU) 520. The micro controller unit may be coupled to an alternator, such as a full-bridge 510 and a sense load 530. In this embodiment, the micro controller unit 520 is configured to sense a sensed voltage across the sense load and to control an operating frequency of a switching voltage driving the piezoelectric device. The micro controller unit 520 may be configured such that, responsive to the sensed voltage, the micro controller unit 520 changes the operating frequency.

Figure 12:
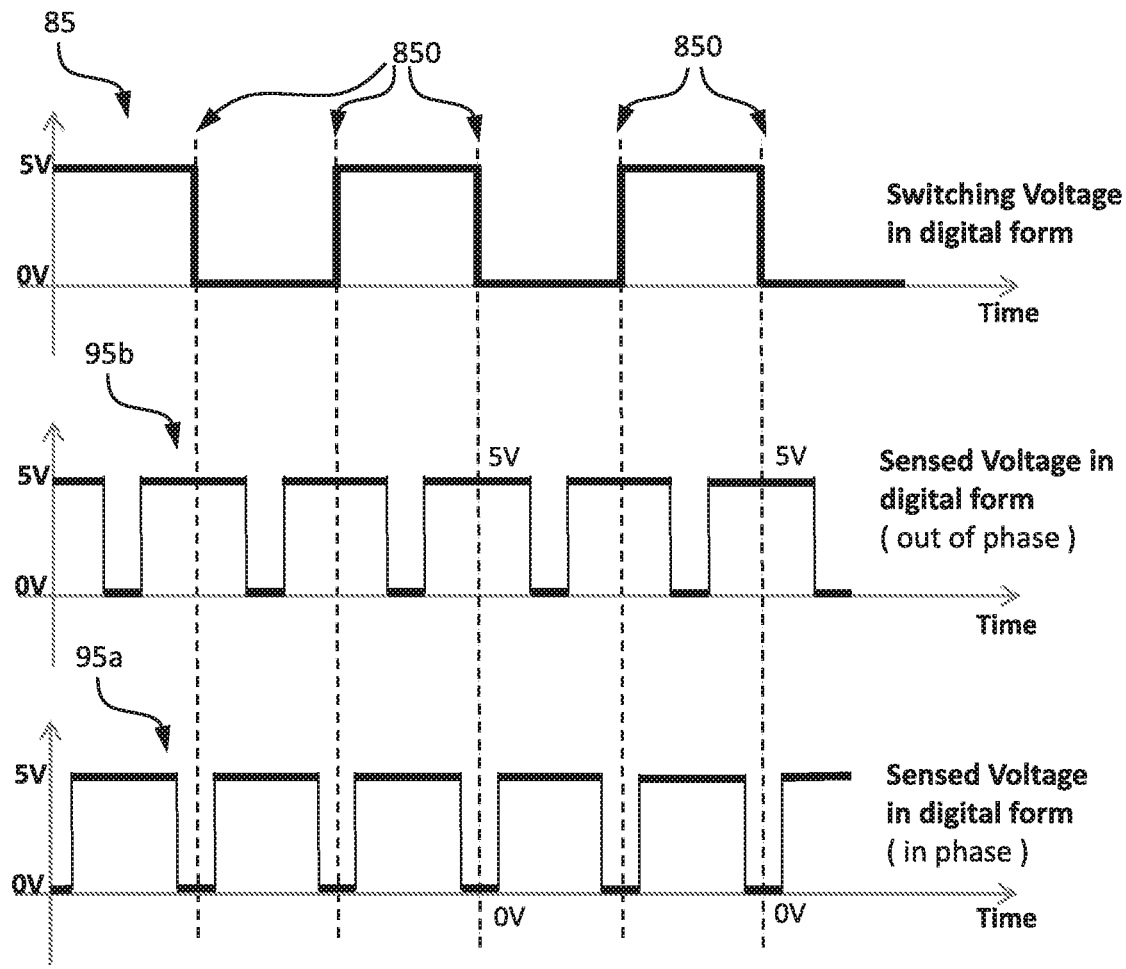
FIG. 12 shows an example of a switching voltage, a sensed voltage out of phase with the switching voltage, and a sensed voltage in phase with the switching voltage.

FIG. 12 illustrates voltages signals applicable to any of the embodiments described above. In FIG. 12, an example of a switching voltage digital signal 85, a sensed voltage digital signal 95a which is in phase with the switching voltage digital signal, and a sensed voltage digital signal 95b which is out of phase with the switching voltage digital signal are illustrated on a common time axis. The driving device according to an embodiment of the present disclosure is configured so that each transition 850 of the switching voltage digital signal 85, the driving device can determine whether the sensed voltage and the switching voltage are in phase or out of phase, relative to each other. For example, in FIG. 12, when a transition 850 of the switching voltage digital signal 85 is found to correspond to (coincide with) a lower voltage state of the sensed voltage digital signal 95a, the sensed voltage may be deemed to be in phase with the switching voltage. Alternatively, for example, in FIG. 12, when a transition 850 of the switching voltage digital signal 85 is found to correspond to (coincide with) a higher voltage state of the sensed voltage digital signal 95*b*, the sensed voltage may be deemed to be out of phase with the switching voltage. Therefore, by sensing or sampling the amplitude of the sensed voltage digital signal 95 at a time corresponding to a transition 850 of the switching voltage digital signal 85, the driving device is able to determine whether or not the sensed voltage is in phase with the switching voltage. The sampling of the amplitude or value of the sensed voltage digital signal 95 may occur at a rising transition of the switching voltage digital signal, or at a falling transition of the switching voltage digital signal. The driving device is further configured to determine whether the piezoelectric device is at or near the target frequency or otherwise, based on whether or not the sensed voltage and the switching voltage have been determined to be in phase or out of phase relative to each other. An alternative embodiment includes a method performed on non-digital signals, wherein the sensed voltage is sampled at one or more transitions of the switching voltage in determining whether the piezoelectric device is operating as desired or otherwise.

Figure 13:
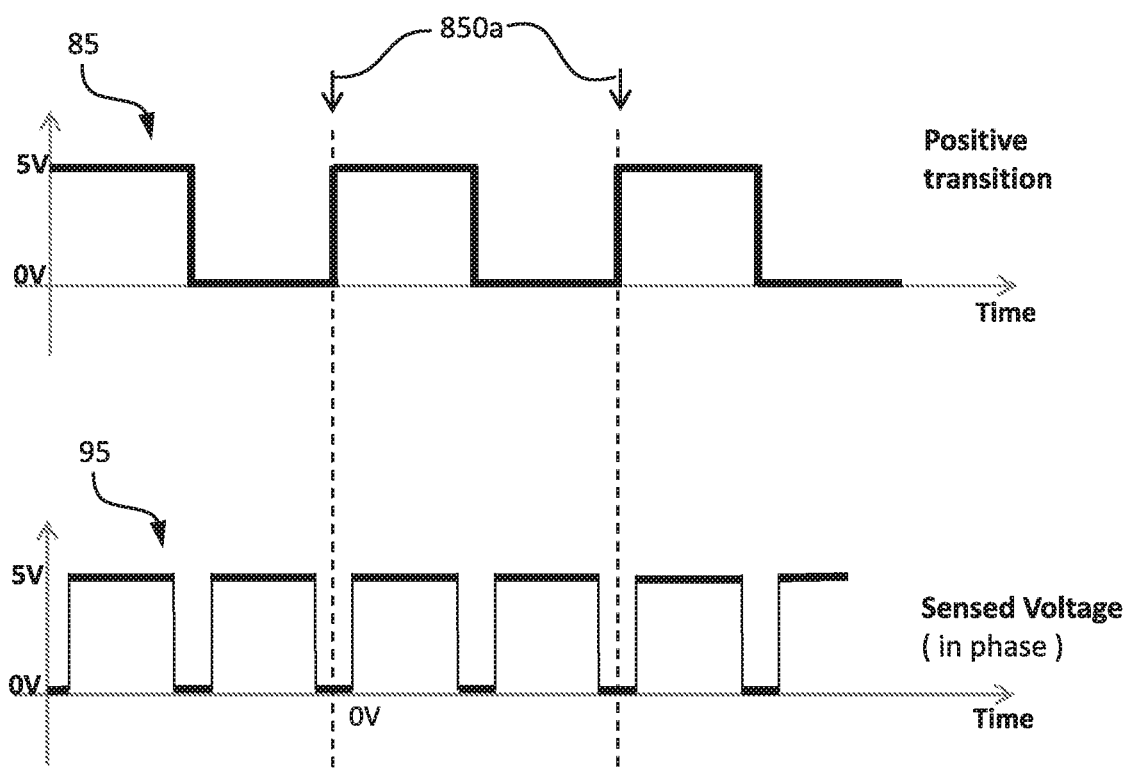
FIG. 13 shows an example of sampling a sensed voltage at a positive transition of a corresponding switching voltage according to an embodiment.
Figure 14:
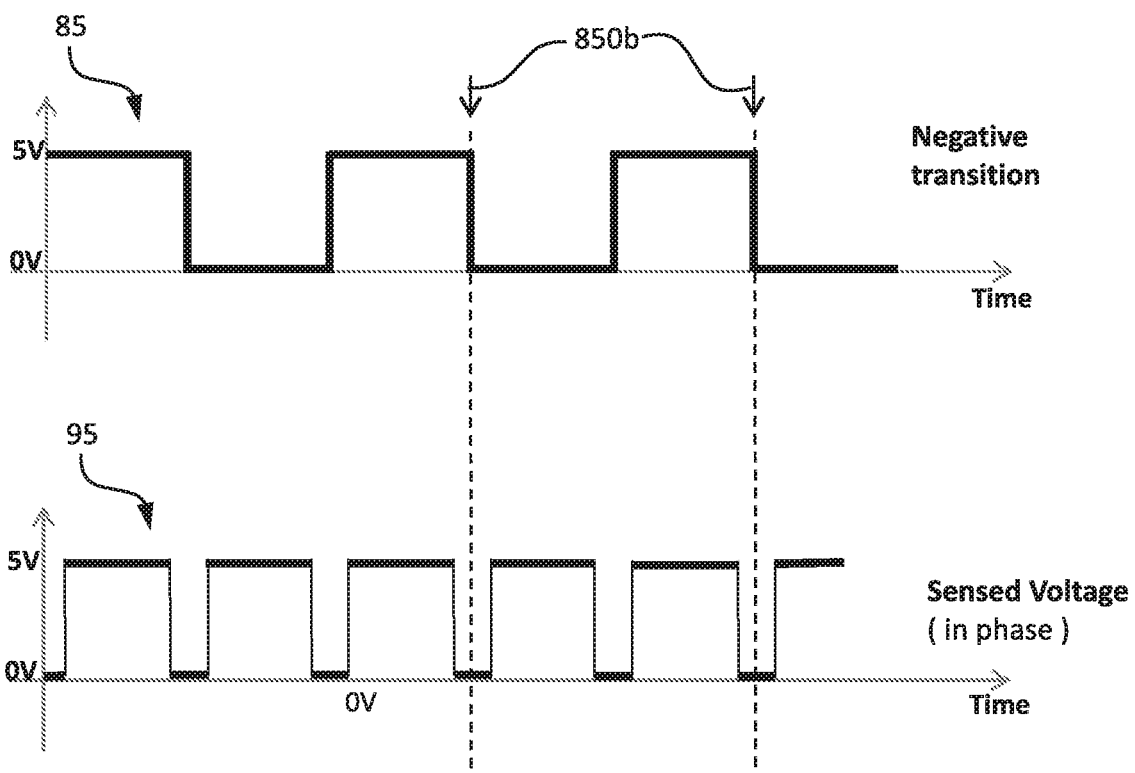
FIG. 14 shows an example of sampling a sensed voltage at a negative transition of a corresponding switching voltage according to another embodiment.
Figure 15:
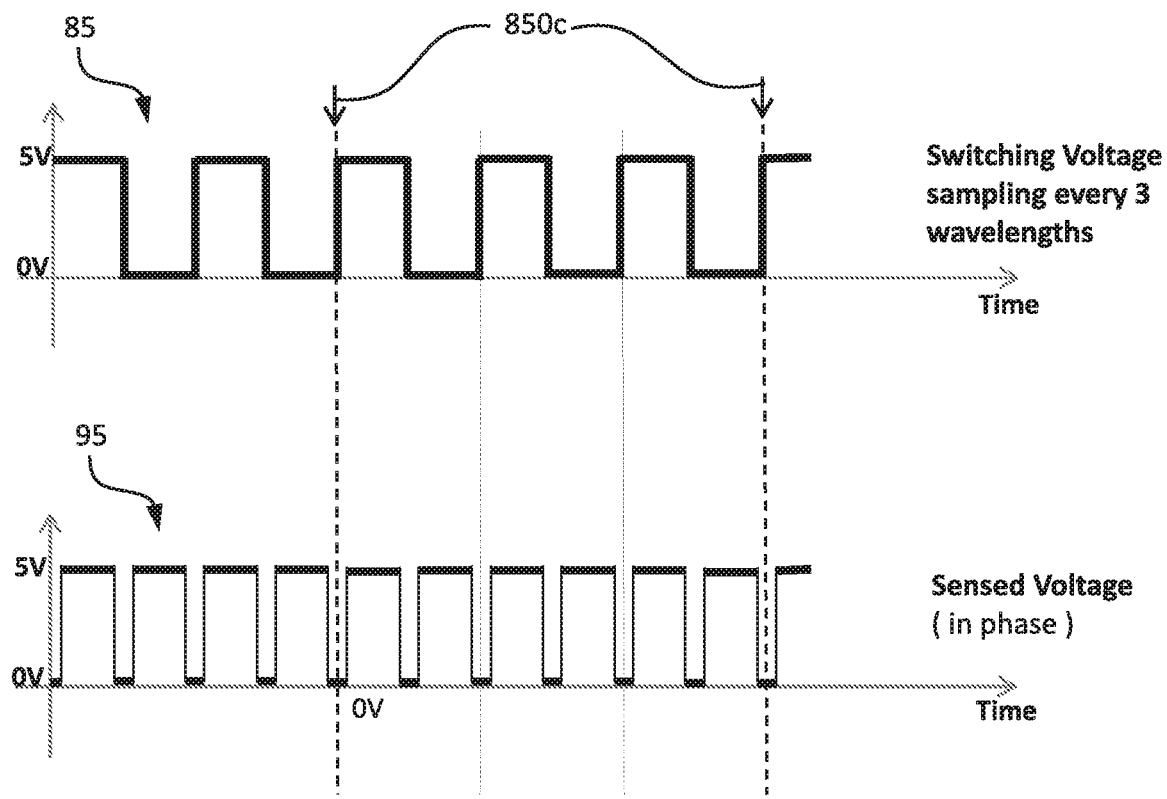
FIG. 15 shows an example of sampling a sensed voltage at every third positive transition of a corresponding switching voltage according to yet another embodiment.
Figure 16:
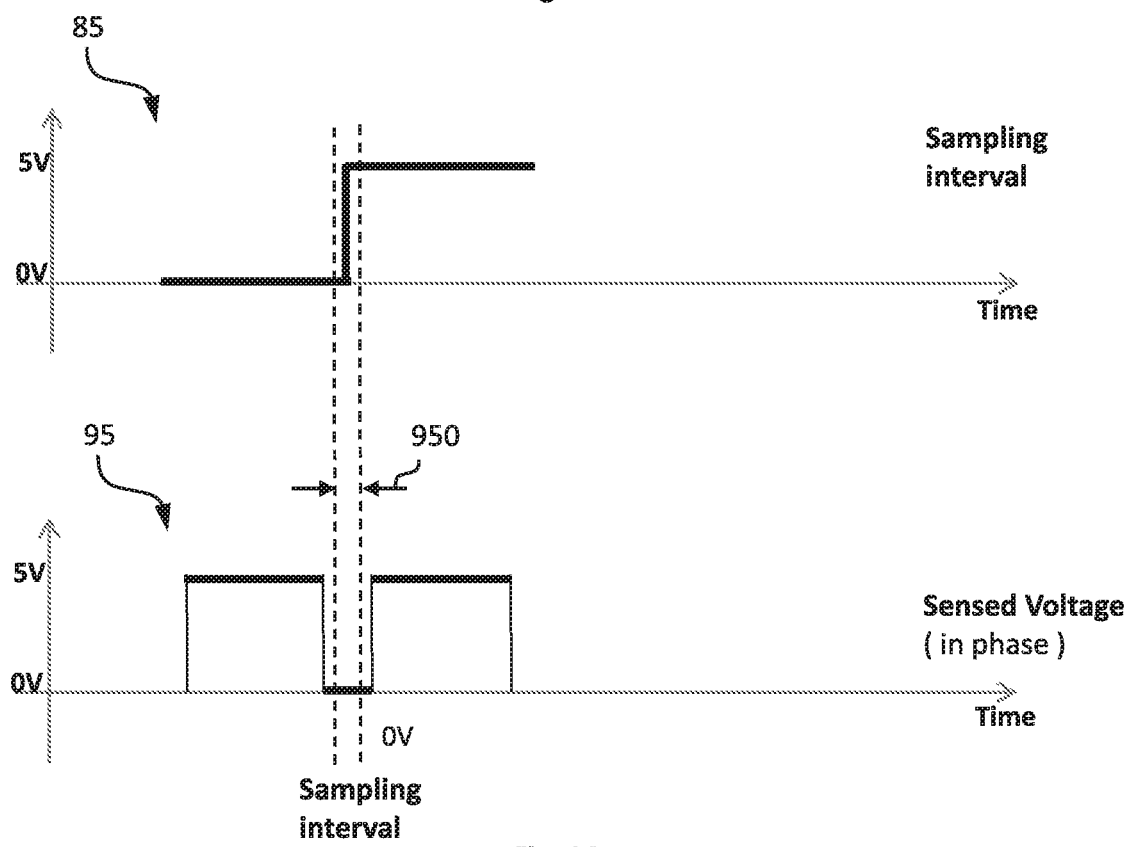
FIG. 16 shows an example of a sampling interval during sampling of a sensed voltage according to an embodiment.

Considering the above, applicable to embodiments such as the atomizer 40 or the driving devices 100/200/300/400/500, the respective logic devices may be configured to sense or sample the sensed voltage 90 and/or the sensed voltage digital signal 95 at a transition 850 of the switching voltage 80 and/or switching voltage digital signal 85. In accordance with embodiments of the present disclosure, the samples obtained can be used in determining if the piezoelectric device is operating at target frequency. In an embodiment as shown in FIG. 13, the sensing or sampling of a sensed voltage digital signal 95 may be triggered or performed periodically, at selected positive (rising) transitions 850*a* of the switching voltage digital signal 85. In another embodiment as shown in FIG. 14, the sensing or sampling of a sensed voltage digital signal 95 may be triggered or performed periodically, at selected negative (falling) transitions 850*b* of the switching voltage digital signal 85. In yet another embodiment as shown in FIG. 15, the sensing or sampling of a sensed voltage digital signal 95 may be triggered or performed at selected non-consecutive transitions 850*c* of the switching voltage digital signal 85. In one embodiment as shown in FIG. 16, the logic device may be configured to sense or sample a sensed voltage digital signal 95 multiple times within a sampling interval 950, and thereafter to determine an average of the multiple sensed values.

Alternatively, one or more of the methods described above may be performed on non-digital signals, wherein the sensed voltage is compared against a logic rule, for example, a polarity of the sensed voltage. Additionally, the sensing or sampling of the sensed voltage or sensed voltage digital signal may be performed at time intervals either periodically or non-periodically, depending on the purpose of the application and/or operating conditions.

In an embodiment, the logic device may be a digital flip flop, and is configured to sense or sample a sensed voltage digital signal 95 upon being triggered by a transition of the switching voltage digital signal 85. Accordingly, at a transition of the switching voltage digital signal 85, the sensed voltage digital signal 95 is sensed or sampled by the digital flip flop. According to a logic rule embodied by the digital flip flop, the digital flip flop provides an output Q to the controller, wherein the output Q acts as an instruction to either increase or decrease an operating frequency of the switching voltage. Optionally, the digital flip flop may also be configured to receive an input of a switching voltage digital signal 85.

Figure 17:
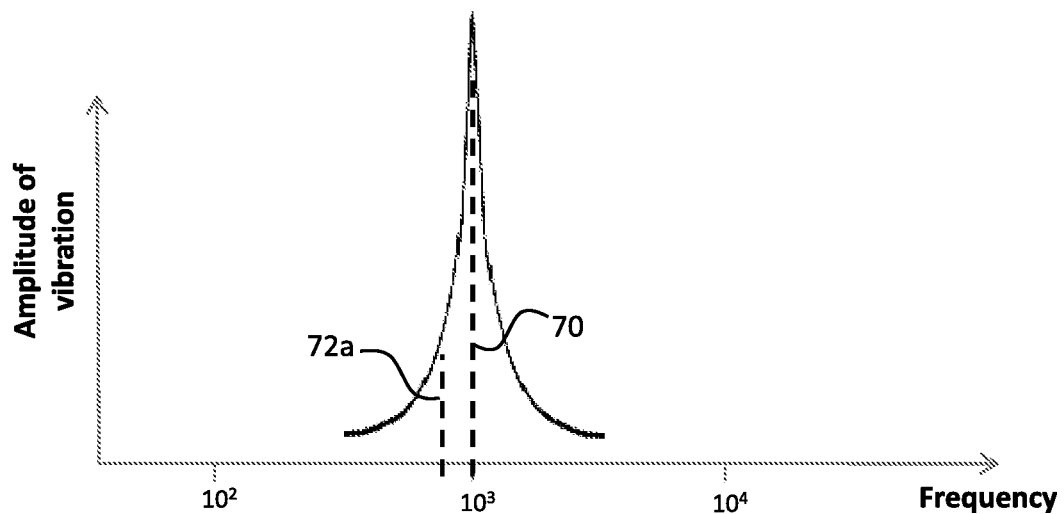
FIG. 17 shows an initial operating frequency lower than a target frequency of a piezoelectric device according to an embodiment.
Figure 18:
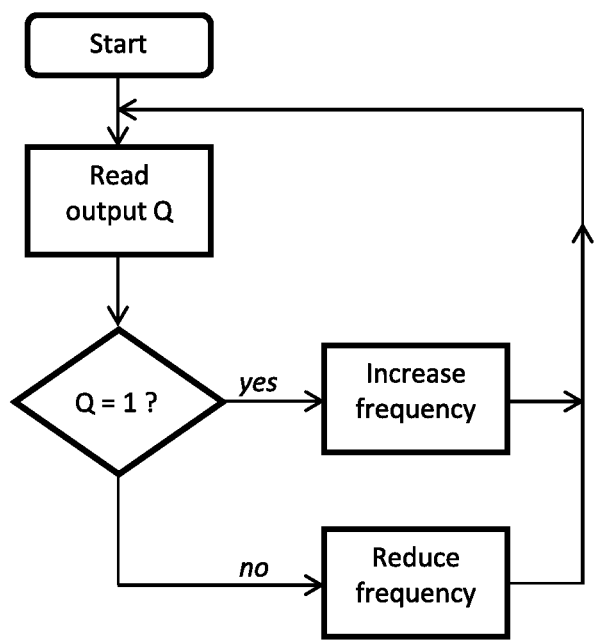
FIG. 18 shows a process flowchart of the logic table according to the embodiment of FIG. 17.

FIGS. 17 to 21 illustrate an exemplary embodiment of the driving device as described above in operation. In the exemplary embodiment as shown in FIG. 17, upon switching on the driving device, the driving device may provide an initial operating frequency which is lower in amplitude than a target frequency 70 associated with the piezoelectric device (in this example, 103 Hz). As shown in FIG. 18, when output Q is equal to a first state (such as equal to "1"), corresponding to the sensed voltage being out of phase with the switching voltage, the controller is configured to increase the operating frequency of the switching voltage. Conversely, when output Q is equal to a second state (not equal to "1") corresponding to the sensed voltage being in phase with the switching voltage, the controller is configured to decrease the operating frequency of the switching voltage.

Figure 19:
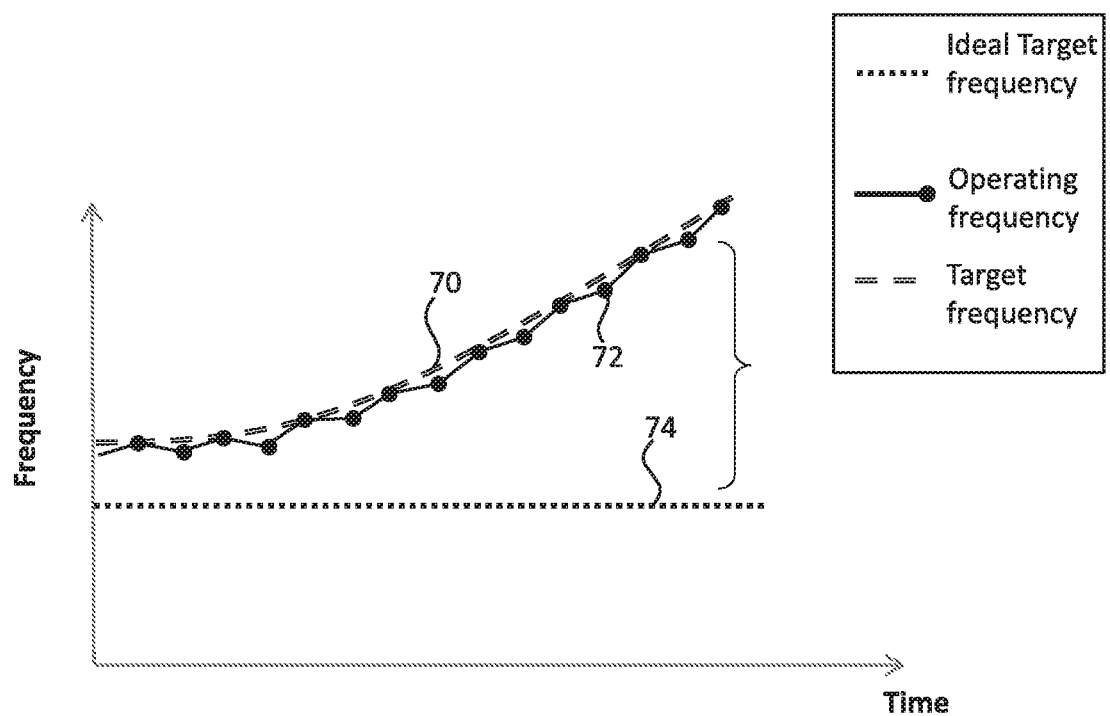
FIG. 19 shows a drift in target frequency of a piezoelectric device and a corresponding operating frequency of the switching voltage according to the embodiment of FIG. 17.
Figure 20:
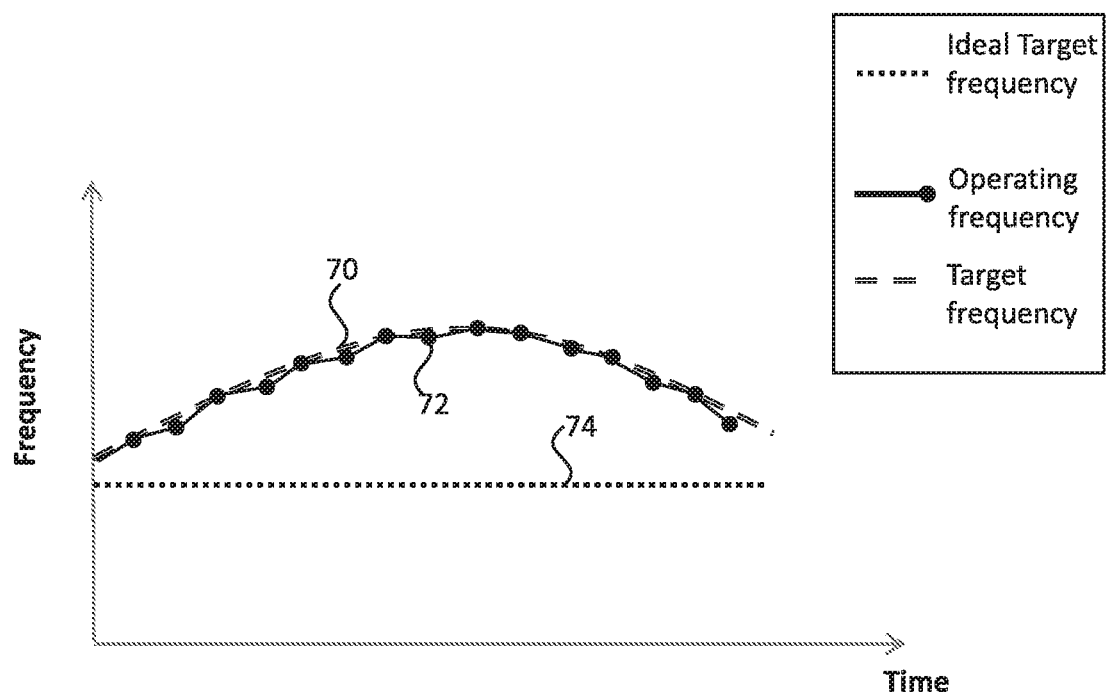
FIG. 20 shows another drift in target frequency of a piezoelectric device and a corresponding operating frequency of the switching voltage according to the embodiment of FIG. 17.

FIG. 19 and FIG. 20 show plots of frequency against time, superimposed and exaggerated to aid understanding. Plot 74 represents an ideal target frequency 74 of a piezoelectric device. In an ideal and hypothetical case, the ideal target frequency would remain constant throughout the operation of the piezoelectric device, so that efficient operation of the piezoelectric device can be easily achieved by setting the operating frequency at the same frequency as the ideal target frequency. However, in actual piezoelectric device operation, self-heating, environmental factors and/or other influences may cause the piezoelectric device to exhibit a target frequency 70 that varies in value over the course of operation of the piezoelectric device. Plot 70 represents one possible behavior of the target frequency in which the target frequency "drifts" or increases over time in the course of operation of the piezoelectric device. Plot 70 of FIG. 20 illustrates another possible example where the target frequency does not vary linearly with respect to time. It is also conceivable that the target frequency may decrease after increasing for a period of time after the piezoelectric device is switched on. Knowing what the target frequency is at any one time can be useful, for example, so that the operating frequency can be set to the same frequency value and the piezoelectric device will perform at a desired level of efficiency. However, oftentimes in actual applications, the target frequency is not known. Without knowing what the target frequency is, it can be a challenge to determine a suitable operating frequency for the piezoelectric device at any one point in time.

Embodiments of the present disclosure address this and other difficulties by providing a driving device configured to drive a piezoelectric device at an operating frequency 72 configured to track a target frequency 70. As shown in FIG. 19 and FIG. 20, the operating frequency can be said to track the target frequency over a period of time when a difference between the operating frequency and the target frequency is less than a predetermined value at any time within the period of time. The operating frequency can be said to track the target frequency over a period of time when the operating frequency is at or near the target frequency throughout the period of time. As the target frequency increases, the operating frequency increases. As the target frequency decreases, the operating frequency decreases. The driving device is configured to keep the operating frequency 72 tracking the target frequency 70, without a preliminary step of determining the value of the target frequency.

In accordance with one embodiment, the driving device is configured to perform a method of increasing the operating frequency 72 from a first operating frequency to a second operating frequency. This may be iteratively performed until the second operating frequency is at or near the target frequency. The second operating frequency may be considered at or near the target frequency when the second operating frequency is within a target frequency band. The target frequency band may be pre-defined as a range of frequencies, in which the range includes at least one resonant frequency (or harmonic) of the piezoelectric device. The driving device is configured to determine if the second operating frequency is within the target frequency band, and to responsively change the operating frequency. If the second operating frequency is lower than a lower bound of the target frequency band, the operating frequency is increased, and this is repeated until the operating frequency reaches/enters target frequency band. The driving device is configured such that, once the operating frequency is determined to be within the target frequency band, the operating frequency will be maintained within or near the target frequency band. The operating frequency can be said to track the target frequency when the operating frequency is within or near the target frequency band.

According to one embodiment, the driving device is configured to perform a method including alternately increasing 72a and decreasing 72b the operating frequency by a predetermined value.

According to one embodiment, the driving device is configured to perform a method including, upon determining that the operating frequency is in or near a target frequency band, repeatedly increasing or decreasing the operating frequency by a predetermined value. Counter-intuitively, the operating frequency 72 is kept repeatedly "moving" towards and/or away from the target frequency 70 even though the operating frequency is already at or near the target frequency.

Thus, it can be appreciated that, according to one embodiment, when the operating frequency is made to track the target frequency, tracking may involve at times increasing a difference between the operating frequency and the target frequency, as well as at times decreasing the difference between the operating frequency and the target frequency. The method may involve periodically changing the operating frequency by the predetermined value. When the target frequency 70 drifts during operation, the change in the target frequency may also contribute towards an increase or a decrease in a difference between the operating frequency and the target frequency. In this or a similar manner of increasing or decreasing the operating frequency, tracking by the operating frequency can be implemented to address the challenges associated with piezoelectric resonant frequency drift. In this embodiment, accordingly to the flow chart logic as shown in FIG. 18, the target frequency 70 may represent a possible upper bound to the operating frequency 72. The target frequency 70 may also represent a possible upper limit to the target frequency band.

Figure 21:
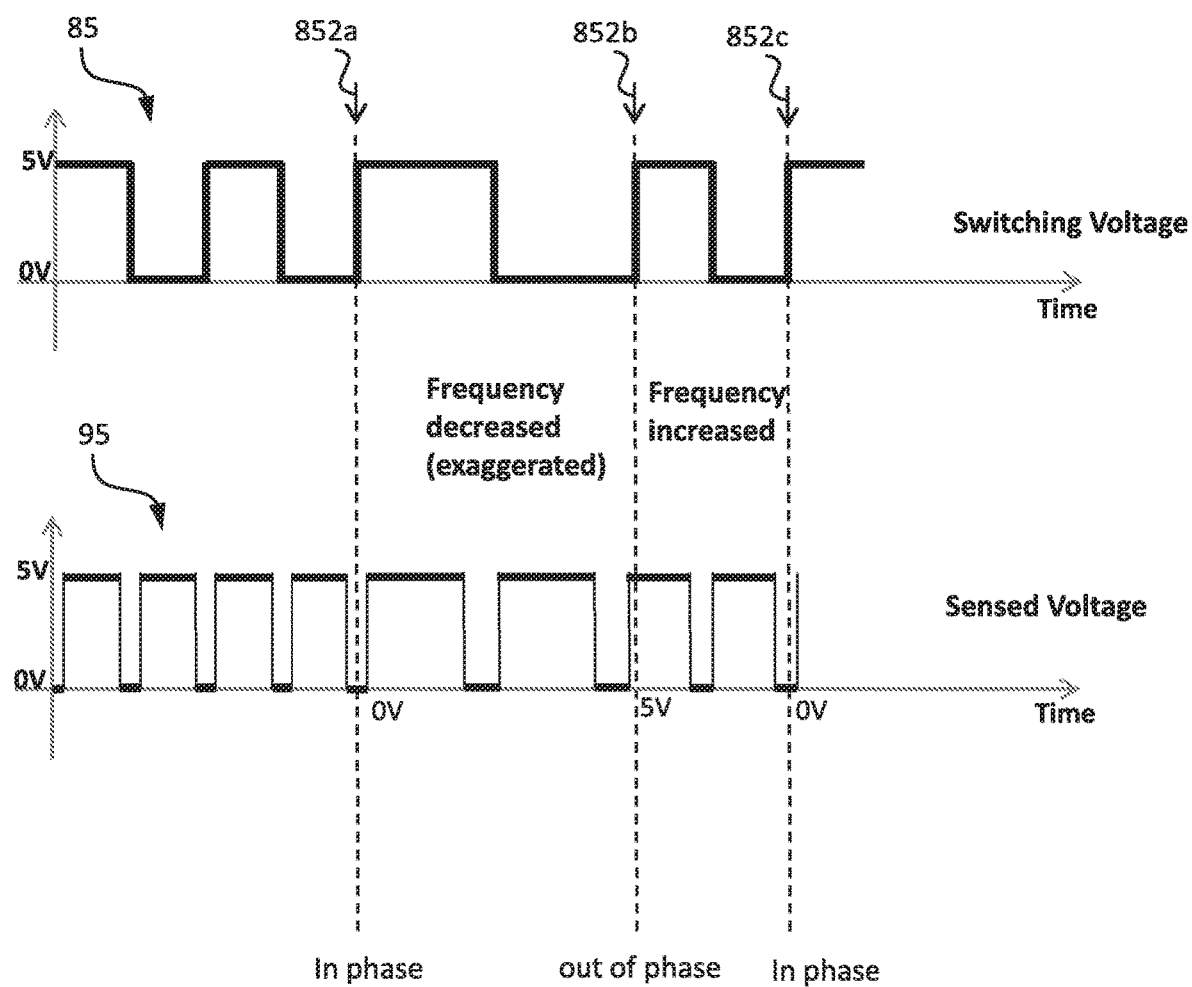
FIG. 21 shows an example of adjustment in a switching voltage and a corresponding sensed voltage according to the embodiment of FIG. 17.

FIG. 21 shows an example of an exaggerated digital signal illustrating a change in operating frequency upon sensing or sampling at consecutive positive transitions 852a/852b/852c. In accordance with one embodiment, the driving device is configured to, at a first positive transition 852a of the switching voltage digital signal, determine the sensed voltage digital signal 95. At this instance, the sensed voltage digital signal is found to be a lower voltage state corresponding to the sensed voltage being in phase with the switching voltage. In response to this, the operating frequency (of the switching voltage) is decreased. At a second positive transition 852b, the sensed voltage digital signal 95 is found to be at a higher voltage state. This is taken to correspond to the sensed voltage being out of phase with the switching voltage. In response, the operating frequency (of the switching voltage) is increased. At a third positive transition 852c, the sensed voltage digital signal 95 is found to correspond to the sensed voltage being in phase with the switching voltage, which in turn triggers a decrease (downward adjustment) in the operating frequency.

Figure 22:
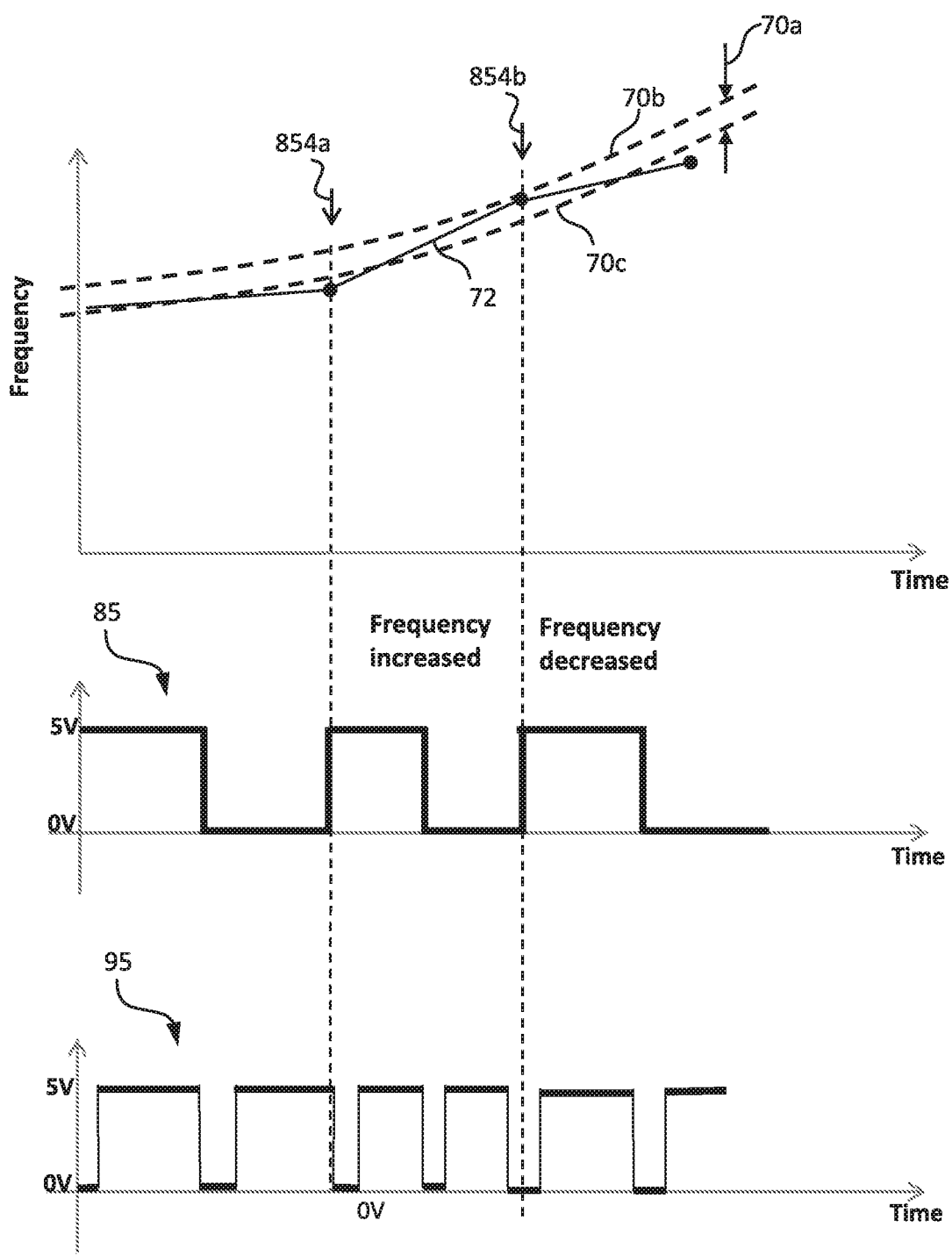
FIG. 22 shows an example of an adjustment in a switching voltage and a target frequency band in the sensed voltage according to an embodiment.

In another embodiment as shown in FIG. 22, the piezoelectric device may define a target frequency band 70a, having an upper limit 70b and a lower limit 70c. When the operating frequency 72 of the switching voltage is within the target frequency band 70a, or between upper limit 70b and lower limit 70c, the piezoelectric device demonstrates peak or near peak amplitude of vibration and efficiency. When the operating frequency 72 is within the target frequency band 70a (which may be inclusive of one or both of the upper limit and the lower limit), the piezoelectric device can be observed to operate efficiently enough for its intended purpose, for example, the resultant piezoelectric vibration is sufficient for atomizing a viscous fluid. As an example, the target frequency band may be a resonance frequency band, or a range of frequency values about a resonant (harmonic) frequency. As an example, the target frequency band may be around +/−100 Hz (hertz) in the neighborhood of a target frequency of about 500 kHz (kilohertz). In another example, the target frequency band may be 100 Hz (hertz), and the target frequency may vary between 100 kHz to 120 kHz at the time when the piezoelectric device begins operations. In yet another example, the target frequency band may be 2 kHz. These examples are given solely to aid understanding.

Optionally, the resolution or size of each change made to the operating frequency may be varied so as to control how closely the operating frequency tracks the target frequency. For example, if each change is sufficiently small relative to the target frequency 70, or is small in relative to a target frequency band 70a, the operating frequency tracks the actual target frequency 70 or target frequency band 70a more closely. This allows the piezoelectric device to appear to be driven at or close to target frequency continuously.

An example of an exaggerated digital signal illustrating the change in operating frequency 72 upon sensing or sampling at consecutive positive transitions 854a/854b is shown in FIG. 22. At a first positive transition 854a, the sensed voltage digital signal 95 corresponds to the sensed voltage being out of phase with the switching voltage. Based on this, the piezoelectric device is sensed to be operating outside the target frequency band 70a. In response, the operating frequency 72 of the switching voltage is increased by a predetermined value. At a second positive transition 854b, the sensed voltage digital signal 95 corresponds to the sensed voltage being in phase with the switching voltage. Based on this, the piezoelectric device is sensed to be operating within the target frequency band 70a. The operating frequency 72 of the switching voltage is decreased by the predetermined value. The upper limit 70b of the target frequency band 70a acts as an upper bound (upper limit) to the operating frequency 72. The predetermined value is equal to or smaller than the target frequency band 70a. The target frequency band may be defined by the difference between the upper limit 70b and the lower limit 70c. It can be appreciated that the operating frequency does not exceed the upper limit 70b. Although the operating frequency 72 is either within the target frequency band 70a or out of the target frequency band 70a in the course of operating over a period of time, it can be observed that in practical implementation, the piezoelectric device continuously performs as desired over the period of time. For example, an atomizer according to one embodiment of the present disclosure can provide a continuous delivery of atomized viscous fluid over a period of time in operation, while over the same period of time the operating frequency may be repeatedly in and out of the target frequency band. For avoidance of doubt, for the purpose of this disclosure, this is one example of the operating frequency tracking the target frequency band or the target frequency.

Figure 23:
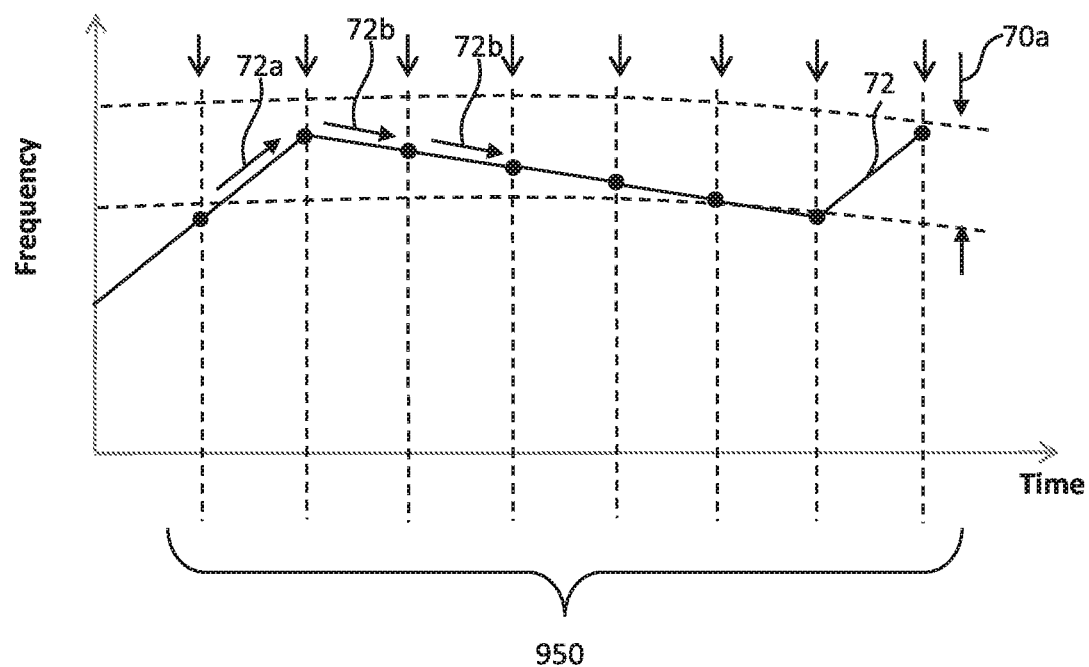
FIG. 23 shows an embodiment of increasing and decreasing of an operating frequency according to an embodiment.

As illustrated in FIG. 23, in an embodiment, over a period of time 950, there may be multiple instances when the sensed voltage is sensed, and a corresponding adjustment is made to the operating frequency. Each adjustment to the operating frequency may be an increase or a decrease. As shown, the size of each decrease 72b in the operating frequency may be smaller than the size of each increase 72a in the operating frequency. In doing so, the operating frequency stays within the target frequency band 70a for a longer duration during the operation of the piezoelectric device while moving out of the target frequency band 70a intermittently. Alternatively, the decrease 72b in the operating frequency 72 may be set to be equal in value to the increase 72a in the operating frequency 72.

Figure 24:
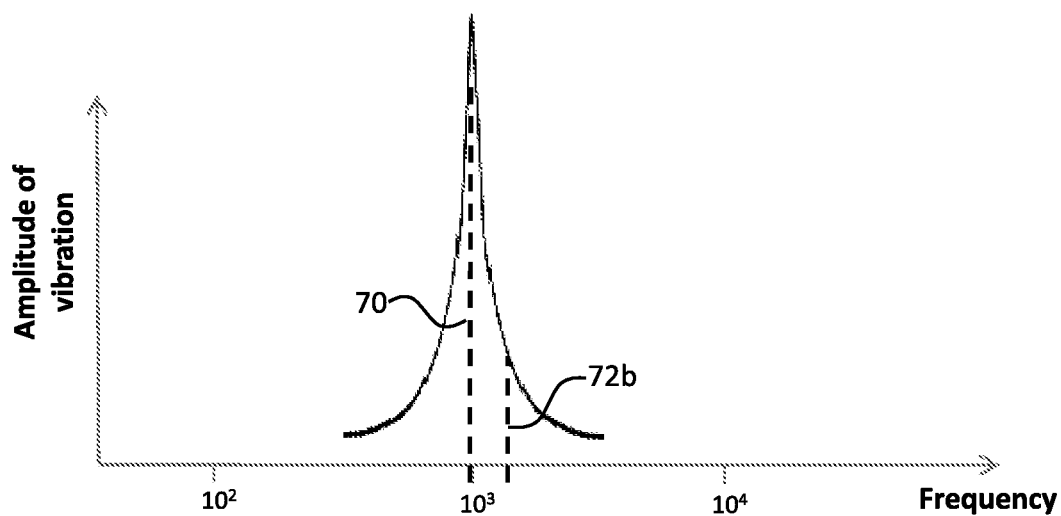
FIG. 24 shows an initial operating frequency higher than a target frequency of a piezoelectric device according to an embodiment.
Figure 25:
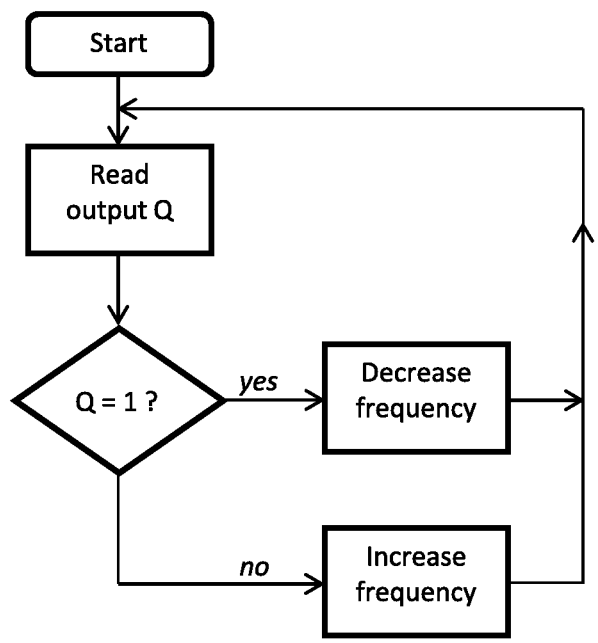
FIG. 25 shows a process flowchart of the logic table according to the embodiment of FIG. 24.
Figure 26:
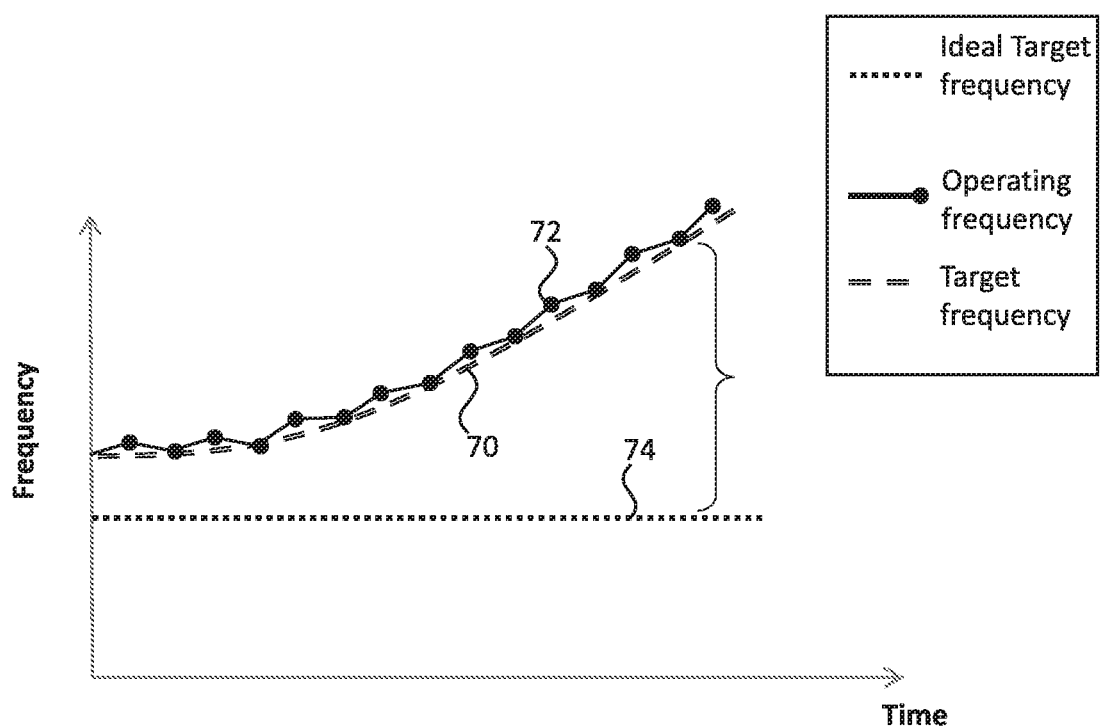
FIG. 26 shows a drift in target frequency of a piezoelectric device and a corresponding operating frequency of the switching voltage according to the embodiment of FIG. 24.
Figure 27:
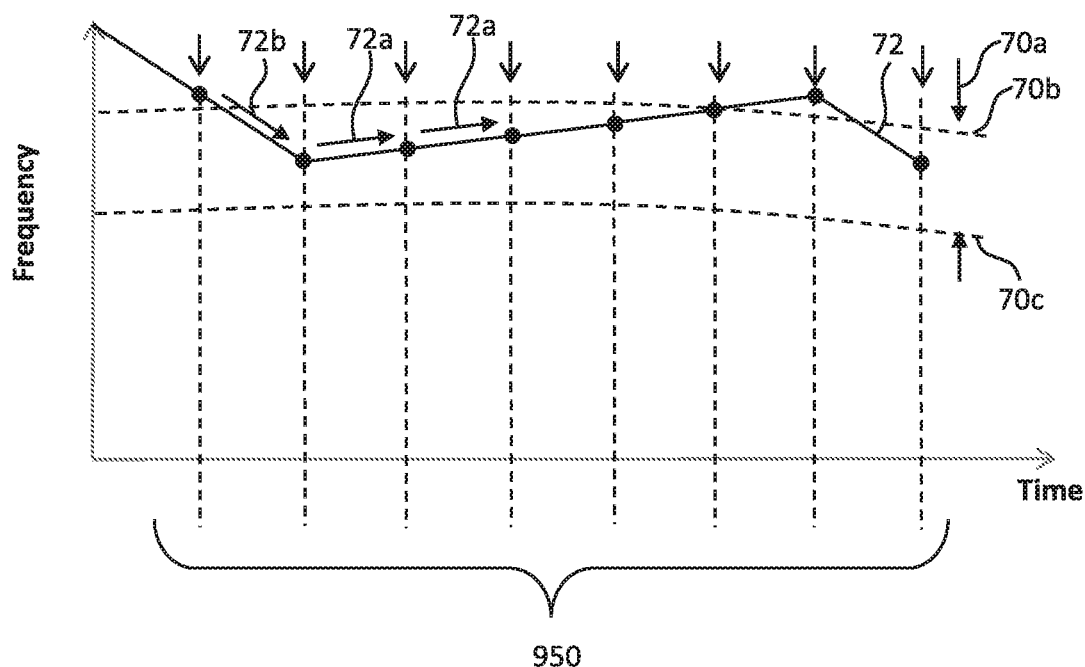
FIG. 27 shows another embodiment of increasing and decreasing of an operating frequency according to an embodiment.

FIGS. 24 to 26 illustrate an exemplary embodiment of the driving device as described above in operation. In the exemplary embodiment as shown in FIG. 24, upon switching on the driving device, the driving device may provide an initial operating frequency 72b which is higher in amplitude than a target frequency 70 associated with the piezoelectric device (in this example, 103 Hz). As shown in FIG. 25, when output Q is equal to a first state (such as equal to "1"), corresponding to the sensed voltage being out of phase with the switching voltage, the controller is configured to decrease the operating frequency of the switching voltage. Conversely, when output Q is equal to a second state (not equal to "1") corresponding to the sensed voltage being in phase with the switching voltage, the controller is configured to increase the operating frequency of the switching voltage.

FIG. 26 shows plots of frequency against time, superimposed and exaggerated to aid understanding. Plot 74 represents an ideal target frequency 74 of a piezoelectric device. In an ideal and hypothetical case, the ideal target frequency would remain constant throughout the operation of the piezoelectric device, so that efficient operation of the piezoelectric device can be easily achieved by setting the operating frequency at the same frequency as the ideal target frequency. However, in actual piezoelectric device operation, self-heating, environmental factors and/or other influences may cause the piezoelectric device to exhibit a target frequency 70 that varies in value over the course of operation of the piezoelectric device. Plot 70 represents one possible behavior of the target frequency in which the target frequency "drifts" or increases over time in the course of operation of the piezoelectric device. It is also conceivable that the target frequency may decrease after increasing for a period of time after the piezoelectric device is switched on. Knowing what the target frequency is at any one time can be useful, for example, so that the operating frequency can be set to the same frequency value and the piezoelectric device will perform at a desired level of efficiency. However, oftentimes in actual applications, the target frequency is not known. Without knowing what the target frequency is, it can be a challenge to determine a suitable operating frequency for the piezoelectric device at any one point in time.

Embodiments of the present disclosure address this and other difficulties by providing a driving device configured to drive a piezoelectric device at an operating frequency 72 configured to track a target frequency 70. As shown in FIG. 26, the operating frequency can be said to track the target frequency over a period of time when a difference between the operating frequency and the target frequency is less than a predetermined value at any time within the period of time. The operating frequency can be said to track the target frequency over a period of time when the operating frequency is at or near the target frequency throughout the period of time. As the target frequency increases, the operating frequency increases. As the target frequency decreases, the operating frequency decreases. The driving device is configured to keep the operating frequency 72 tracking the target frequency 70, without a preliminary step of determining the value of the target frequency.

In accordance with one embodiment, the driving device is configured to perform a method of decreasing the operating frequency 72 from a first operating frequency to a second operating frequency. This may be iteratively performed until the second operating frequency is at or near the target frequency. The second operating frequency may be considered at or near the target frequency when the second operating frequency is within a target frequency band. The target frequency band may be pre-defined as a range of frequencies, in which the range includes at least one resonant frequency (or harmonic) of the piezoelectric device. The driving device is configured to determine if the second operating frequency is within the target frequency band, and to responsively change the operating frequency. If the second operating frequency is higher than an upper bound of the target frequency band, the operating frequency is decreased, and this is repeated until the operating frequency reaches/enters target frequency band. The driving device is configured such that, once the operating frequency is determined to be within the target frequency band, the operating frequency will be maintained within or near the target frequency band. The operating frequency can be said to track the target frequency when the operating frequency is within or near the target frequency band.

According to one embodiment, the driving device is configured to perform a method including alternately increasing 72a and decreasing 72b the operating frequency by a predetermined value. According to one embodiment, the driving device is configured to perform a method including, upon determining that the operating frequency is in or near a target frequency band, repeatedly increasing or decreasing the operating frequency by a predetermined value. Counter-intuitively, the operating frequency 72 is kept repeatedly "moving" towards and/or away from the target frequency 70 even though the operating frequency is already at or near the target frequency. Thus, it can be appreciated that, according to one embodiment, when the operating frequency is made to track the target frequency, tracking may involve at times increasing a difference between the operating frequency and the target frequency, as well as at times decreasing the difference between the operating frequency and the target frequency. The method may involve periodically changing the operating frequency by the predetermined value. When the target frequency 70 drifts during operation, the change in the target frequency may also contribute towards an increase or a decrease in a difference between the operating frequency and the target frequency. In this or a similar manner of increasing or decreasing the operating frequency, tracking by the operating frequency can be implemented to address the challenges associated with piezoelectric resonant frequency drift. In this embodiment, accordingly to the flow chart logic as shown in FIG. 25, the target frequency 70 may represent a possible lower bound to the operating frequency 72. The target frequency 70 may also represent a possible lower limit to the target frequency band.

Figure 28:
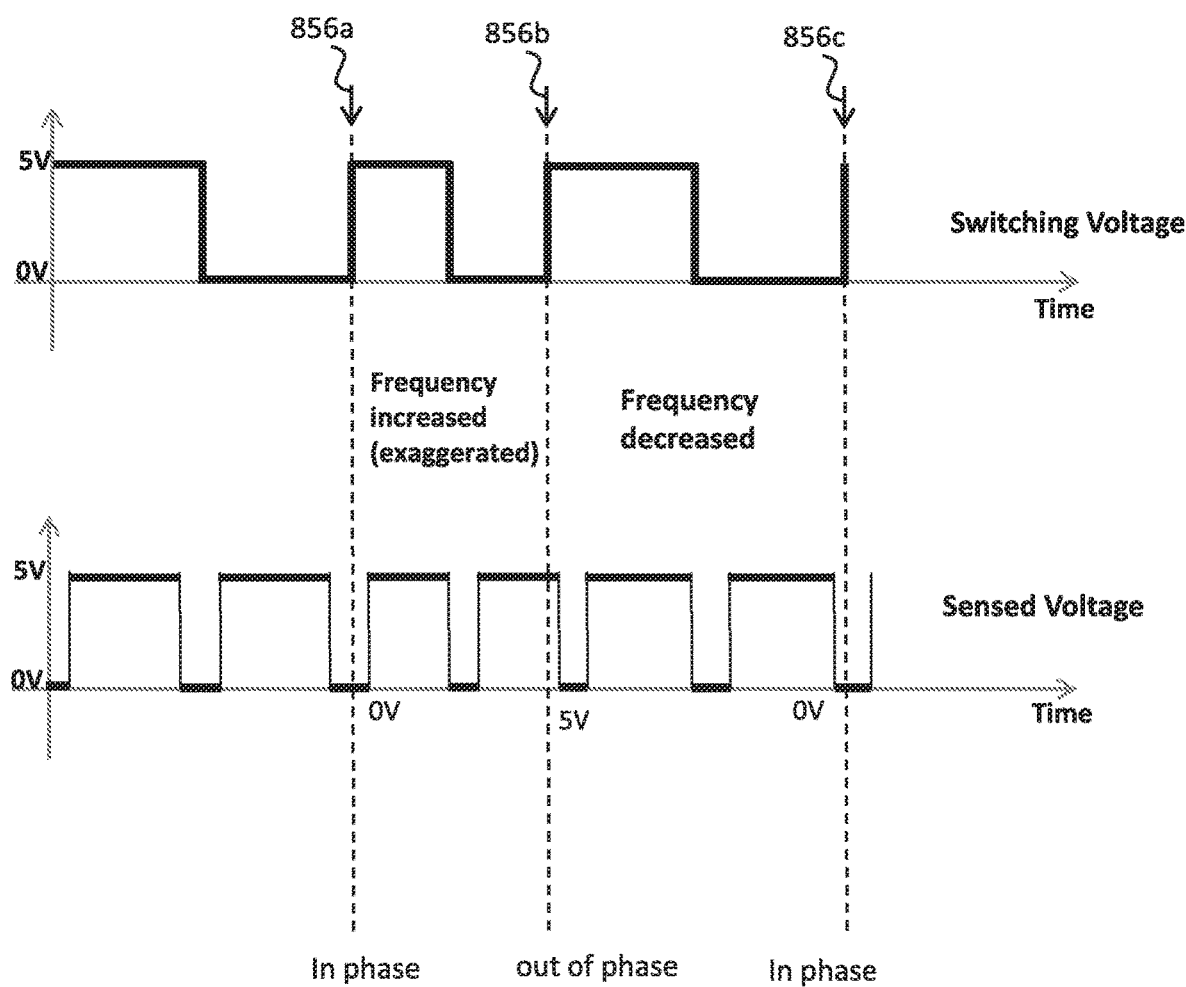
FIG. 28 shows an example of adjustment in a switching voltage and a corresponding sensed voltage according to the embodiment of FIG. 24.

FIG. 28 shows an example of an exaggerated digital signal illustrating a change in operating frequency upon sensing or sampling at consecutive positive transitions 856a/856b/856c. In accordance with one embodiment, the driving device is configured to, at a first positive transition 856a of the switching voltage digital signal, determine the sensed voltage digital signal 95. At this instance, the sensed voltage digital signal is found to be a lower voltage state corresponding to the sensed voltage being in phase with the switching voltage. In response to this, the operating frequency (of the switching voltage) is increased. At a second positive transition 856b, the sensed voltage digital signal 95 is found to be at a higher voltage state. This is taken to correspond to the sensed voltage being out of phase with the switching voltage. In response, the operating frequency (of the switching voltage) is decreased. At a third positive transition 856c, the sensed voltage digital signal 95 is found to correspond to the sensed voltage being in phase with the switching voltage, which in turn triggers an increase (upward adjustment) in the operating frequency.

Optionally, the resolution or size of each change made to the operating frequency may be varied so as to control how closely the operating frequency tracks the target frequency. For example, if each change is sufficiently small relative to the target frequency 70, or is small in relative to a target frequency band 70a, the operating frequency tracks the actual target frequency 70 or target frequency band 70a more closely. This allows the piezoelectric device to appear to be driven at or close to target frequency continuously.

The following continues the example where the driving device provides an initial operating frequency 72a which is higher than a target frequency 70 associated with the piezoelectric device. Upon a first trigger, the sensed voltage digital signal corresponds to the sensed voltage being out of phase with the switching voltage. Based on this, the piezoelectric device is sensed to be operating outside the target frequency band. In response, the operating frequency of the switching voltage is decreased by a predetermined value. Upon a second trigger, the sensed voltage digital signal corresponds to the sensed voltage being in phase with the switching voltage. Based on this, the piezoelectric device is sensed to be operating within the target frequency band. The operating frequency of the switching voltage is increased by the predetermined value. The lower limit of the target frequency band acts as a lower bound (lower limit) to the operating frequency. The predetermined value is equal to or smaller than the target frequency band. The target frequency band may be defined by the difference between the upper limit and the lower limit. It can be appreciated that the operating frequency does not fall below the lower limit in this example. Although the operating frequency is either within the target frequency band or out of the target frequency band in the course of operating over a period of time, it can be observed that in practical implementation, the piezoelectric device continuously performs as desired over the period of time. For example, an atomizer according to one embodiment of the present disclosure can provide a continuous delivery of atomized viscous fluid over a period of time in operation, while over the same period of time the operating frequency may be repeatedly in and out of the target frequency band. For avoidance of doubt, for the purpose of this disclosure, this is one example of the operating frequency tracking the target frequency band or the target frequency.

In an embodiment, over a period of time, there may be multiple instances when the sensed voltage is sensed, and a corresponding adjustment is made to the operating frequency. Each adjustment to the operating frequency may be an increase or a decrease. The size of each increase in the operating frequency may be smaller than the size of each decrease in the operating frequency. In doing so, the operating frequency stays within the target frequency band for a longer duration during the operation of the piezoelectric device while moving out of the target frequency band intermittently. Alternatively, the decrease in the operating frequency may be set to be equal in value to the increase in the operating frequency.

Figure 29A:
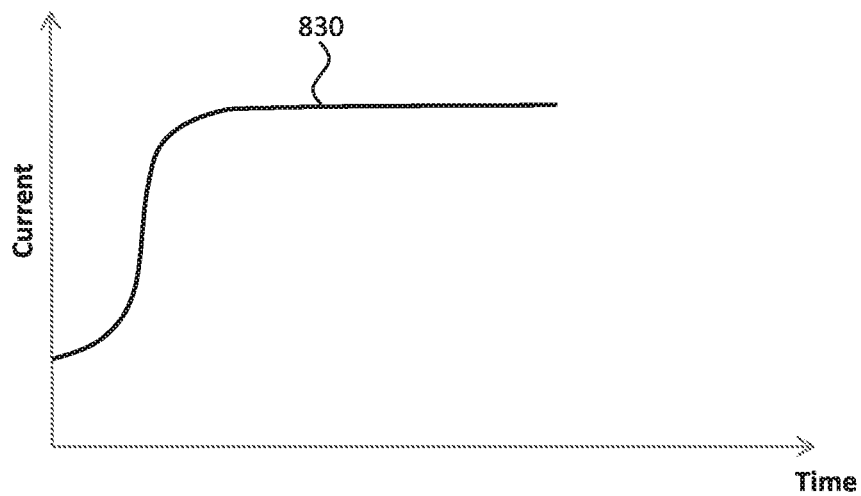
FIG. 29A and FIG. 29B shows a plot show plots of current drawn by a piezoelectric device for atomizing a fluid according to an embodiment different embodiments.
Figure 29B:
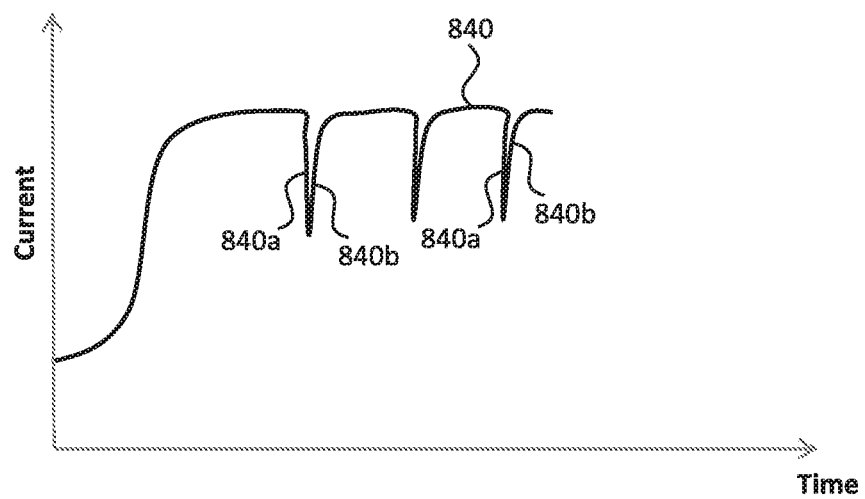

Referring to FIG. 29A, an example of a current 830 drawn by a piezoelectric device as described in the atomizer 40 or a piezoelectric device driven by the driving devices 100/200/300/400/500 is shown. Upon switching on the atomizer 40 or driving device 100/200/300/400/500, it can be seen that the current drawn by the piezoelectric device increases and thereafter upon an operating frequency driving the piezoelectric device is close to or at a target frequency, the current remains constantly at a high value. Although the target frequency drifts in time due to self-heating, environmental changes, etc. the operating frequency tracks the drift accordingly, hence allowing the current drawn by the piezoelectric device to remain high and relatively constant. This enables a consistent high amplitude of vibration output from the piezoelectric device and therefore constant atomizing of a viscous fluid. Conversely, FIG. 29B illustrates a current 840 drawn by a piezoelectric device driven by another device whereby the device periodically scans or sweeps for changes in target frequency, and thereafter adjusts an operating frequency accordingly. Therefore, the current 840 drawn experiences periodic drops 840a and recoveries 840b, and hence a non-consistent amplitude of vibration and therefore atomizing of fluid.

In one embodiment, an atomizer having a piezoelectric device is configured such that an operating frequency is adjustable in a step-wise manner to increase or to decrease the operating frequency, in which the amount adjusted in each step is predetermined, and in which the operating frequency is increased if the piezoelectric device is in phase with the operating frequency, and in which the operating frequency is decreased if the piezoelectric device is out of phase with the operating frequency. The operating frequency is adjustable by a discrete amount to either increase or decrease the operating frequency, the size of the discrete amount being predetermined. The size of the discrete amount is independent of a difference between the operating frequency and the target frequency. The size of the discrete amount is independent of a difference between the operating frequency and the target frequency band. The size of the discrete amount is independent of a difference between the operating frequency and an upper limit of the target frequency band. The size of the discrete amount is independent of a difference between the operating frequency and a lower limit of the target frequency band.

Figure 30:
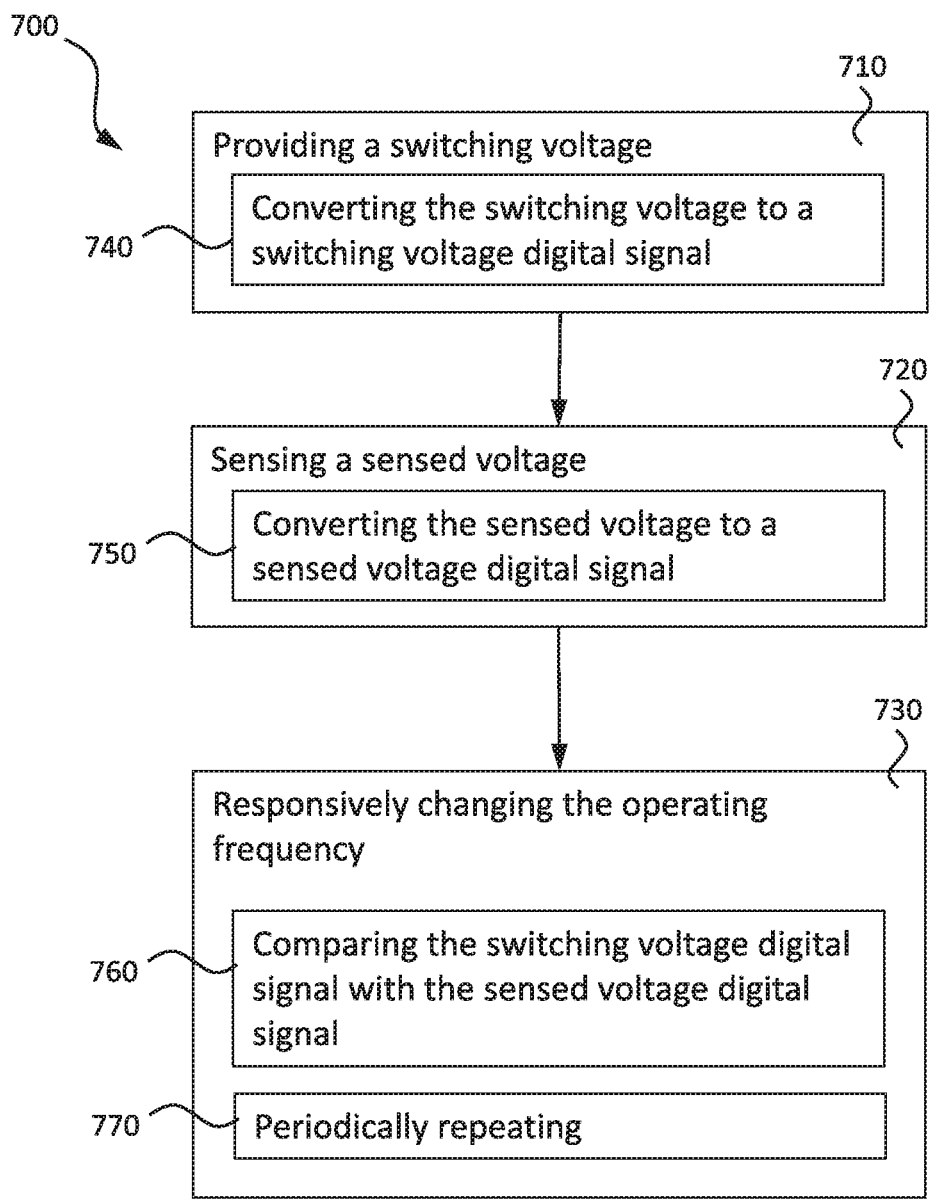
FIG. 30 shows a flowchart of a method of driving a piezoelectric device.
Figure 31:
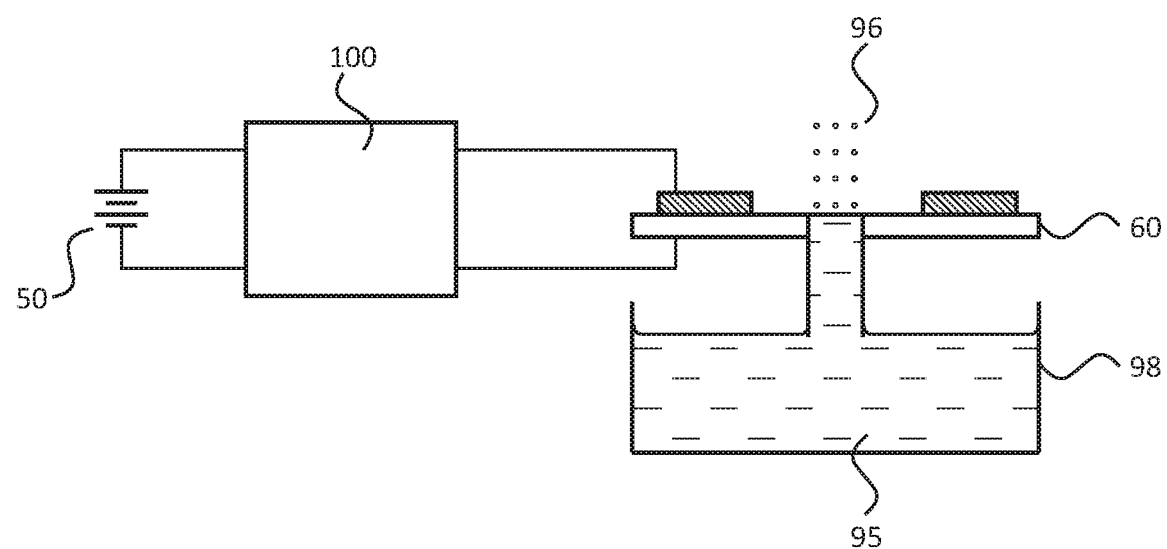
FIG. 31 shows one embodiment of the atomizer invention, comprising: a power source 50, a circuit board 100, a piezoelectric component 60, a reservoir 98 for holding the liquid 95 or substance to be atomized or vaporized 96.

FIG. 30 illustrates a method 700 of driving a piezoelectric device. The method includes providing a switching voltage across the piezoelectric device at an operating frequency (710), sensing a sensed voltage corresponding to a phase of the piezoelectric device (720). and responsive to whether the sensed voltage is in phase or out of phase relative to the switching voltage, changing the operating frequency provided to the piezoelectric device (730). The change to the operating frequency is one selected from: (a) increasing the operating frequency by a first value, and (b) decreasing the operating frequency by a second value. The amount (quantum or absolute value) of change to the operating frequency is predetermined or independent of whether the sensed voltage is in phase or out of phase relative to the switching voltage. Regardless of the whether the sensed voltage is in phase or out of phase relative to the switching voltage, a change to the operating frequency is made.

Optionally and additionally, the method may include converting the switching voltage to a switching voltage digital signal (740) having at least one transition between two states; and using the at least one transition to trigger the sensing of the sensed voltage. The method may further include converting the sensed voltage to a sensed voltage digital signal (750). The method may further include, comparing the switching voltage digital signal with the sensed voltage digital signal (760) to determine whether the sensed voltage is in phase or out of phase relative to the switching voltage. The method may further include periodically repeating at a sampling frequency (770). The resulting operating frequency tracks a target frequency band to provide a desired performance of the piezoelectric device.

An atomizer for a liquid comprising: a housing; a power source; a piezoelectric device operable by a switching voltage; and a circuit including a sense load, the sense load being operably coupled to the piezoelectric device so that a sensed voltage across the sense load has a phase corresponding to a phase of the piezoelectric device, the circuit being configured to: determine whether the sensed voltage is in phase or out of phase relative to the switching voltage; responsive to the sensed voltage being in phase relative to the switching voltage when the switching voltage is provided at an operating frequency, make a change to the operating frequency by a predetermined first value; and responsive to the sensed voltage being out of phase relative to the switching voltage when the switching voltage is provided at the operating frequency, make a change to the operating frequency by a predetermined second value, wherein if the predetermined first value corresponds to an increase in value of the operating frequency, the predetermined second value corresponds to a decrease in value of the operating frequency, and wherein if the predetermined first value corresponds to a decrease in value of the operating frequency, the predetermined second value corresponds to an increase in value of the operating frequency; the circuit is configured to perform the following repeatedly:

determine whether the sensed voltage is in phase or out of phase relative to the switching voltage; and make a corresponding change to the operating frequency by one of the predetermined first value and the predetermined second value; the circuit is configured to make the corresponding change to the operating frequency periodically according to a sampling frequency, such that the operating frequency fluctuates within a target frequency band, wherein the target frequency band is a predefined range of frequencies including at least one resonant frequency of the piezoelectric device; the sampling frequency is defined by selected transitions of the switching voltage; the circuit further comprises: an alternator coupled to the piezoelectric device, the alternator being configured to provide the switching voltage to drive the piezoelectric device; and an analog digital converter configured to convert the switching voltage to a switching voltage digital signal; and a logic device configured such that the selected transitions between two states of the switching voltage digital signal triggers the sensing of the sensed voltage and the corresponding change to the operating frequency by one of the predetermined first value and the predetermined second value; the alternator comprises a full-bridge configured to produce the switching voltage in the form of a square waveform.

The alternator can be configured in a push-pull configuration such that the switching voltage is a square waveform, and the sense load is a resistive element; the circuit is further configured to: determine a first occurrence when the operating frequency is within a target frequency band, the target frequency band being a predefined range of frequencies including at least one resonant frequency of the piezoelectric device; responsive to the first occurrence, repeatedly perform the following: determine whether the sensed voltage is in phase or out of phase relative to the switching voltage; and make a corresponding change to the operating frequency by one of the predetermined first value and the predetermined second value; the circuit is configured to make the corresponding change to the operating frequency such that the operating frequency fluctuates within the target frequency band; the corresponding changes to the operating frequency are made at times corresponding to selected transitions of the switching voltage; each of the predetermined first value and the predetermined second value is smaller than a range of the target frequency band;

wherein during operation of the atomizer, each of the predetermined first value and the predetermined second value is independent of a difference in value between the operating frequency and either one of an upper limit of the target frequency band and a lower limit of the target frequency band; and wherein during operation of the atomizer, each of the predetermined first value and the predetermined second value is independent of a difference in value between the operating frequency and the at least one resonant frequency.

The atomizer can also have source of liquid or fluid, wherein the piezoelectric device in operation being configured to transmit energy to provide a non-intermittent stream of atomized fluid over a period of operation, and wherein the operating frequency changes over the period of operation.

The atomizer's circuit can be further configured to: determine a first occurrence when the operating frequency is within a target frequency band, the target frequency band being a predefined range of frequencies including at least one resonant frequency of the piezoelectric device; responsive to the first occurrence, repeatedly perform the following: determine whether the sensed voltage is in phase or out of phase relative to the switching voltage; and make a corresponding change to the operating frequency by one of the predetermined first value and the predetermined second value; the circuit can be configured to make the corresponding change to the operating frequency such that the operating frequency fluctuates within the target frequency band; the corresponding changes to the operating frequency can be made at times corresponding to selected transitions of the switching voltage; each of the predetermined first value and the predetermined second value is smaller than a range of the target frequency band. Wherein during operation of the atomizer, each of the predetermined first value and the predetermined second value can be independent of a difference in value between the operating frequency and either one of an upper limit of the target frequency band and a lower limit of the target frequency band, and wherein during operation of the atomizer, each of the predetermined first value and the predetermined second value can be independent of a difference in value between the operating frequency and the at least one resonant frequency. The atomizer being configured to atomize the liquid, wherein the piezoelectric device in operation is configured to transmit energy to the liquid so as to provide a non-intermittent stream of atomized liquid over a period of operation, and wherein the operating frequency changes over the period of operation.

Detailed embodiments of the present invention are disclosed; however, the disclosed embodiments are merely exemplary of the invention, which can be embodied in various forms; specific structural and functional details disclosed are not to be interpreted as limiting, but merely as a basis for the claims and as a representative basis for teaching one skilled in the art to variously employ the present invention in virtually any appropriately detailed structure. The title, headings, terms and phrases used are not intended to limit the subject matter or scope; but rather, to provide an understandable description of the invention. The invention is composed of several sub-parts that serve a portion of the total functionality of the invention independently and contribute to system level functionality when combined with other parts of the invention. The terms "a" or "an" are defined as: one or more than one. The term "plurality" is defined as: two or more than two. The term "another" is defined as: at least a second or more. The terms "including" and/or "having" are defined as comprising (i.e., open language). The term "coupled" is defined as connected, although not necessarily directly, and not necessarily mechanically.

Any element in a claim that does not explicitly state "means for" performing a specific function, or "step for" performing a specific function, is not be interpreted as a "means" or "step" clause as specified in 35 U.S.C. Sec. 112, Paragraph 6. In particular, the use of "step of" in the claims herein is not intended to invoke the provisions of 35 U.S.C. Sec. 112, Paragraph 6.

Incorporation by Reference: All publications, patents, patent applications and Internet website addresses mentioned in this specification are incorporated by reference to the same extent as if each individual publication, patent, or patent application was specifically and individually indicated to be incorporated by reference:

U.S. Pat. Nos. 9,149,588B2; 4,689,515A; 4,715,353A; US20200060337A1; U.S. Pat. No. 7,855,606B2; US20090295455A1; U.S. Ser. No. 10/603,683B2; CN102526848A; U.S. Pat. Nos. 5,113,116A; 7,119,475B2; 7,034,800B2; US20090099485A1.

We claim:

1. An atomizer for a liquid comprising:

a housing;

a power source;

a piezoelectric device operable by a switching voltage; and a circuit including a sense load, the sense load being operably coupled to the piezoelectric device so that a sensed voltage across the sense load has a phase corresponding to a phase of the piezoelectric device, the circuit being configured to:

determine whether the sensed voltage is in phase or out of phase relative to the switching voltage;

responsive to the sensed voltage being in phase relative to the switching voltage when the switching voltage is provided at an operating frequency, make a change to the operating frequency by a predetermined first value; and responsive to the sensed voltage being out of phase relative to the switching voltage when the switching voltage is provided at the operating frequency, make a change to the operating frequency by a predetermined second value, wherein if the predetermined first value corresponds to an increase in value of the operating frequency, the predetermined second value corresponds to a decrease in value of the operating frequency, and wherein if the predetermined first value corresponds to a decrease in value of the operating frequency, the predetermined second value corresponds to an increase in value of the operating frequency.

2. The atomizer as recited in claim 1, wherein the circuit is configured to perform the following repeatedly:

determine whether the sensed voltage is in phase or out of phase relative to the switching voltage; and make a corresponding change to the operating frequency by one of the predetermined first value and the predetermined second value.

3. The atomizer as recited in claim 2, wherein the circuit is configured to make the corresponding change to the operating frequency periodically according to a sampling frequency, such that the operating frequency fluctuates within a target frequency band, wherein the target frequency band is a predefined range of frequencies including at least one resonant frequency of the piezoelectric device.

4. The atomizer as recited in claim 3, wherein the sampling frequency is defined by selected transitions of the switching voltage.

5. The atomizer as recited in claim 4, wherein the circuit further comprises:

an alternator coupled to the piezoelectric device, the alternator being configured to provide the switching voltage to drive the piezoelectric device; and an analog digital converter configured to convert the switching voltage to a switching voltage digital signal; and a logic device configured such that the selected transitions between two states of the switching voltage digital signal triggers the sensing of the sensed voltage and the corresponding change to the operating frequency by one of the predetermined first value and the predetermined second value.

6. The atomizer as recited in claim 5, wherein the alternator comprises a full-bridge configured to produce the switching voltage in the form of a square waveform.

7. The atomizer as recited in claim 5, wherein the alternator is configured in a push-pull configuration such that the switching voltage is a square waveform.

8. The atomizer as recited in claim 7, wherein the sense load is a resistive element.

9. The atomizer as recited in claim 1, wherein the circuit is further configured to:

determine a first occurrence when the operating frequency is within a target frequency band, the target frequency band being a predefined range of frequencies including at least one resonant frequency of the piezoelectric device;

responsive to the first occurrence, repeatedly perform the following:

determine whether the sensed voltage is in phase or out of phase relative to the switching voltage; and make a corresponding change to the operating frequency by one of the predetermined first value and the predetermined second value.

10. The atomizer as recited in claim 9, wherein the circuit is configured to make the corresponding change to the operating frequency such that the operating frequency fluctuates within the target frequency band.

11. The atomizer as recited in claim 10, wherein the corresponding changes to the operating frequency are made at times corresponding to selected transitions of the switching voltage.

12. The atomizer as recited in claim 11, wherein each of the predetermined first value and the predetermined second value is smaller than a range of the target frequency band.

13. The atomizer as recited in claim 12, wherein during operation of the atomizer, each of the predetermined first value and the predetermined second value is independent of a difference in value between the operating frequency and either one of an upper limit of the target frequency band and a lower limit of the target frequency band.

14. The atomizer as recited in claim 12, wherein during operation of the atomizer, each of the predetermined first value and the predetermined second value is independent of a difference in value between the operating frequency and the at least one resonant frequency.

15. The atomizer as recited in claim 1, the atomizer being configured to atomize the liquid, wherein the piezoelectric device in operation is configured to transmit energy to the liquid so as to provide a non-intermittent stream of atomized liquid over a period of operation, and wherein the operating frequency changes over the period of operation.

16. The atomizer as recited in claim 1, further comprising:
a source of fluid, wherein the piezoelectric device in operation being configured to transmit energy to provide a non-intermittent stream of atomized fluid over a period of operation, and wherein the operating frequency changes over the period of operation.

17. An atomizer for a liquid comprising:
a housing;
a power source;
a piezoelectric device operable by a switching voltage; and
a circuit including a sense load, the sense load being operably coupled to the piezoelectric device so that a sensed voltage across the sense load has a phase corresponding to a phase of the piezoelectric device, the circuit being configured to:
determine whether the sensed voltage is in phase or out of phase relative to the switching voltage;
responsive to the sensed voltage being in phase relative to the switching voltage when the switching voltage is provided at an operating frequency, make a change to the operating frequency by a predetermined first value; and
responsive to the sensed voltage being out of phase relative to the switching voltage when the switching voltage is provided at the operating frequency, make a change to the operating frequency by a predetermined second value,
wherein if the predetermined first value corresponds to an increase in value of the operating frequency, the predetermined second value corresponds to a decrease in value of the operating frequency, and
wherein if the predetermined first value corresponds to a decrease in value of the operating frequency, the predetermined second value corresponds to an increase in value of the operating frequency;
the circuit is configured to perform the following repeatedly:
determine whether the sensed voltage is in phase or out of phase relative to the switching voltage; and
make a corresponding change to the operating frequency by one of the predetermined first value and the predetermined second value;
the circuit is configured to make the corresponding change to the operating frequency periodically according to a sampling frequency, such that the operating frequency fluctuates within a target frequency band, wherein the target frequency band is a predefined range of frequencies including at least one resonant frequency of the piezoelectric device;
the sampling frequency is defined by selected transitions of the switching voltage;
the circuit further comprises:
an alternator coupled to the piezoelectric device, the alternator being configured to provide the switching voltage to drive the piezoelectric device; and
an analog digital converter configured to convert the switching voltage to a switching voltage digital signal; and
a logic device configured such that the selected transitions between two states of the switching voltage digital signal triggers the sensing of the sensed voltage and the corresponding change to the operating frequency by one of the predetermined first value and the predetermined second value;
the alternator comprises a full-bridge configured to produce the switching voltage in the form of a square waveform.

18. The atomizer as recited in claim 17, wherein the alternator is configured in a push-pull configuration such that the switching voltage is a square waveform, and the sense load is a resistive element.

19. The atomizer as recited in claim 17, wherein the circuit is further configured to:
determine a first occurrence when the operating frequency is within a target frequency band, the target frequency band being a predefined range of frequencies including at least one resonant frequency of the piezoelectric device;
responsive to the first occurrence, repeatedly perform the following:
determine whether the sensed voltage is in phase or out of phase relative to the switching voltage; and
make a corresponding change to the operating frequency by one of the predetermined first value and the predetermined second value.

20. The atomizer as recited in claim 19, wherein the circuit is configured to make the corresponding change to the operating frequency such that the operating frequency fluctuates within the target frequency band;
the corresponding changes to the operating frequency are made at times corresponding to selected transitions of the switching voltage;
each of the predetermined first value and the predetermined second value is smaller than a range of the target frequency band;
wherein during operation of the atomizer, each of the predetermined first value and the predetermined second value is independent of a difference in value between the operating frequency and either one of an upper limit of the target frequency band and a lower limit of the target frequency band; and
wherein during operation of the atomizer, each of the predetermined first value and the predetermined second value is independent of a difference in value between the operating frequency and the at least one resonant frequency.

\* \* \* \* \*